(12) United States Patent
Neff et al.

(10) Patent No.: US 7,034,205 B2
(45) Date of Patent: Apr. 25, 2006

(54) GENETICALLY MODIFIED PLANTS HAVING MODULATED BRASSINOSTEROID SIGNALING

(75) Inventors: Michael M. Neff, St. Louis, MO (US); Joanne Chory, Del Mar, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 406 days.

(21) Appl. No.: 09/992,901

(22) Filed: Nov. 14, 2001

(65) Prior Publication Data

US 2002/0073446 A1 Jun. 13, 2002

Related U.S. Application Data

(62) Division of application No. 09/527,073, filed on Mar. 16, 2000, now Pat. No. 6,534,313.

(60) Provisional application No. 60/172,832, filed on Dec. 20, 1999, provisional application No. 60/170,931, filed on Dec. 14, 1999, provisional application No. 60/124,570, filed on Mar. 16, 1999.

(51) Int. Cl.
*C12N 15/82* (2006.01)
*A01H 5/00* (2006.01)
*A01H 5/10* (2006.01)

(52) U.S. Cl. .................. 800/290; 800/298; 435/468
(58) Field of Classification Search ................ 435/419, 435/468; 800/279, 282, 290, 298
See application file for complete search history.

(56) References Cited

FOREIGN PATENT DOCUMENTS

WO 95/16041 6/1995

OTHER PUBLICATIONS

Mangold et al. Gene and cDNA for plant cytochrome P450 proteins (CYP72 family) from Catharanthus roseus, and transgenic expression of the gene and a cDNA in tobaco and *Arabidopsis thaliana*. Plant Science, 1994, vol. 96, pp. 129-136.*
Persans et al.Differential induction of cytochrome P450-mediated triasulfuron metabolism by naphthalic anhydride and triasulfuron.Plant Physiol. Dec. 1995;109(4):1483-90.*
Lyznik et al.Heat-inducible expression of FLP gene in maize cells.Plant J. Aug. 1995;8(2):177-86.*
Mitzutani et al. Cytochrome P450 superfamily in *Arabidopsis thaliana*: isolation of cDNAs, differential expression, and RFLP mapping of multiple cytochromes P450. Plant Mol Biol. 1998 May;37(1):39-52.*
Werck-Reichhart D. and Feyereisen P., Cytochromes P450: a success story. Genome Biol. 2000;1(6):3003.1-3003.9.*
Schlichting I. et al., The catalytic pathway of cytochrome p450cam at atomic resolution. Science. Mar. 3, 2000; 287 (5458):1615-22.*
Rupasinghe S. et al. Common active site architecture and binding strategy of four phenylpropanoid P450s from *Arabidopsis thaliana* as revealed by molecular modeling. Protein Eng. Oct. 2003; 16(10):721-31.*
Mangold et al. Gene and cDNA for plant cytochrome P450 proteins (CYP72 family) from *Catharanthus roseus*, and transgenic expression of the gene and a cDNA in tobaco and *Arabidopsis thaliana*. Plant Science, 1994, vol. 96, pp. 129-136.*
Persans et al.Differential induction of cytochrome P450-mediated triasulfuron metabolism by napthalic anhydride and triasulfuron.Plant Physiol. Dec. 1995;109(4):1483-90.*
Lyznik et al.Heat-inducible expression of FLP gene in maize cells.Plant J. Aug. 1995;8(2):177-86.*
Mast N. et al. Broad substrate specificity of human cytochrome P450 46A1 which initiates cholesterol degradation in the brain. Biochemistry. Dec. 9, 2003;42(48):14284-92.*
Shimada Y. et al. Brassinosteroid-6-oxidases from *Arabidopsis* and tomato catalyze multiple C-6 oxidations in brassinosteroid biosynthesis. Plant Physiol. Jun. 2001;126 (2):770-9.*
Baier et al., *The Plant 2-Cys peroxiredoxin BAS1 is a Nuclear-Encoded Chloroplast Protein: Its Expressional Regulation, Phylogenetic Origin, and Implications for its Specific Physiological Function in Plants*, The Plant Journal, vol. 12(1):179-190 (1997).
Bishop et al., *the Tomato Dwarf Gene Isolated by Heterologous Transposon Tagging Encodes the First Meeting Member of a New Cytochrome P450 Family*, The Plant Cell, vol. 8:959-969 (Jun. 1996).
Neff et al., *BAS1: A Gene Regulating Brassinosterid Levels and Light Responsiveness in Arabidopsis*, PNAS vol. 96 (26):15316-15323 (1999).
Doerks, *Protein Annotation: Detective Work for Function Prediction*. TIG, vol. 14 No. 6. pp. 248-250 (1998).
GenBank Accession TO4442, (Nov. 1997).
Rounsley et al., Genbank Accession B29839 (Oct. 1997).
Altmann, Thomas "A tale of dwarfs and drugs: brassinosteroids to the rescue", *Trends in Genetics*, 14(12): 490-495 (1998).
Choe, et al., "the DWF4 Gene of *Arabidopsis* Encodes a Cytochrome P450 that mediates multiple 22α-Hydroxylation Steps in Brassinosteroid Biosynthesis", *The Plant Cell*, 10(2):231-243 (1998).

(Continued)

*Primary Examiner*—Cynthia Collins
(74) *Attorney, Agent, or Firm*—Morrison&Foerster LLP

(57) ABSTRACT

Disclosed are plants and methods of making plants that have a dwarf stature in comparison to wildtype plants. By transforming a wildtype plant with a "bas1" gene, or functional homolog thereof, the plant grows to have a dwarf stature.

29 Claims, 7 Drawing Sheets

OTHER PUBLICATIONS

Szekeres, et al., "Brassinosteroids Rescue the Deficiencyof CYP90, a Cytochrome P450, Controlling Cell Elongation and De-etiolation in *Arabidopsis*", *Cell*, 85:171-182 (1996).

Winkler, et al., "The Maize Dwarf3 Gene Encodes a Cytochrome P450-Mediated Early Step in Gibberellin Biosynthesis", *The Plant Cell*, 7(8):1307-1317 (1995).

Salchert, et al., "Control of cell elongation and stress responses by steroid hormones and carbon catabolic repression in plants", *Philosophical Transactions of the Royal Society of London, Series B*, 353(1374):1517-1520 (1998).

Irmler, Stefan et al., (2000) "Indole Alkaloid Biosynthesis in *Catharanthus roseus*: New Enzyme Activities and Identification of Cytochrome P450 CYP72A1 as Secologanin Synthase" *the Plant Journal*, 24(6): 797-804.

Rupasinghe, Sanjeewa et al., (2003) "Common Active Site Architecture and Binding Strategy of Four Phenylpropanoid P450s from *Arabidopsis thaliana* as revealed by molecular Modeling" *Protein Engineering*, 16(10):721-731.

Schlichting, Ilme et al., (2000) "The Catalytic Pathway of Cytochrome P450cam at Atomic Resolution" *Science*, 287: 1615-1622.

Turk, Edward M. et al., (2003) CYP72B1 Inactivates Brassinosteroid Hormones: An Intersection Between Photomorphogenesis and Plant Steroid Signal Transduction *Plant Physiology*, 133:1643-1653.

Werck-Reichhart, Daniéle et al., (2000) "Cytochromes P450: A Success Story" *Genome Biology*, 1(6):3003.1-3003. 9.

* cited by examiner

FIGURE 1A
bas1 nucleotide sequence (SEQ ID NO: 1)

ATGGAGGAAGAAGTAGCAGCTGGTTCATTCCAAAGGTTCTTGTTCTGTCTGTAATCTTAAGTCTTGTAATAGTGAAGGG
TATGTCTCTGTTATGGTGGAGACCAAGAAGAAGATTGAAGAACATTTCTCTAAACAAGAATTCGAGGTCCTCTTATCATT
TCTTCATCGGAAATGTTAAAGAACTTGTTGGAATGATGCTTAAAGCTTCTTCTCTATGCCTTTCTCTCACAATATT
CTTCCTAGAGTTCTCTCTCTTTTACCATCACTGGAGAAAAATCTACGGTGCTACATTTCTGGTTTGGTTCGGTCCAACTTT
CCGGTTAACGGTAGCCGATCCTGATTTGATCAGAGAGATCTCTCTAAGTCTGAGTTCTACGAGAAGAATGAAGCTCACC
CTTTGGTTAAACAACTTGAAGGCGATGGACTACTTAGTCTCAAAGGTGAAAAATGGGCTCATCGAAAAATCATTAGC
CCTACTTTTCATATGGAGAAAACGGTGAAGTTGAGGTAGATGTCTATGAGTGGTTTCAGATTTTGACTGGTGATAAATGGTC
GAACAGCTTTTGGAAGTAGCTATGAAGATGTCGAGCAGTTTTTCGACTTCAAGCTCAACAATGCTCTTCTTTGTGCTGAA
GCTTTTCAAAAAGTCGTTGTTGAAGCTGATAGAGCGGGCGAGACAAAACGCTATAGAGGGAAGGGAAGAATGTAAGGAGC
GATAAGGAAGTCGTTGTTGAAGCTGATAGAGCGGGCGAGACAAAACGCTATAGAGTGGAGAAGGGAAGAATGTAAGGAGC
CGGCGCGAAGATTGTTGGGATTAATGATTCAGGCAAAGAATGTGACGTGGACGACCATCTTGCTATCTGCACCCGAGTGGCA
TTTTCTTCGCCGGGAAACAGACAACTTCAGGGTCTGATGAGGTCCTCAGGCTCGCGGCTCTGCGGCTCGCCTACCAAGGAC
GGCCAAAGCACGTGATGAGGTCCTCAGGGTCTGATGAGCTACGATTCGACGCGCTAAATCGGATGTG
CGTTGAGTATGATCtgAACGAGTCTTTAAGGTTGTATCGACGAGTTCTATCCACCAATAGTAGCTACGATTCGACGCGCTAAATCGGATGTG
AAGCTAGGAGGGTACAAAATCCCATGTGGCACGGAGCTTCTAATCCAATCATAGCGGTCCATCATGACCAAGCCATTTG
GGGTAATGACGTGAACGAATTCAATCCAGCGAGCTTCTTGCGCACGGAGAATCTTGCGTCTATACTTCAGGCCAAATTGACACTCGCTGTAATG
TACCGTTTGGCCTCGAGTTCACTTGGCACTTGGCTACATGCATCGCATCGAGCTTCA
ATCCAACGCTTCACCTTTCACTTGGCTACATGGTCGTCTATACTTCAGGCCAAATTGACACTCGCTGTAATG
TGCACCAATCACCTTCCGGAGATTGACCAATCATGAGGATTGA

FIGURE 1B
Bas1 amino acid sequence
SEQ ID NO:2 bas1 amino acid sequence

MEEESSSWFIPKVLVLSVILSLVIVKGMSLLWWRPRKIEEHFSKQGIRGPPYHFFIGNVKELVGMMLKASSHPMPFSHNI
LPRVLSFYHHWRKIYGATFLVWFGPTFRLTVADPDLIREIFSKSEFYEKNEAHPLVKQLEGDGLLSLKGEKWAHHRKIIS
PTFHMENLKLLVPVVLKSVTDMVDKWSDKLSENGEVEVDVYEWFQILTEDVISRTAFGSSYEDGRAVFRLQAQQMLLCAE
AFQKVFIPGYRFFPTRGNLKSRKLDKEIRKSLLKLIERRRQNAIDGEGEECKEPAAKDLLGLMIQAKNVTVQDIVEECKS
FFFAGKQTTSNLLTWTTILLSMHPEWQAKARDEVLRVCGSRDVPTKDHVVKLKTLSMILNESLRLYPPIVATIRRAKSDV
KLGGYKIPCGTELLIPIIAVHHDQAIWGNDVNEFNPARFADGVPRAAKHPVGFIPFGLGVRTCIGQNLAILQAKLTLAVM
IQRFTFHLAPTYQHAPTVLMLLYPQHGAPITFRRLTNHED

FIGURE 1C
PROMOTER SEQUENCE Bas1
(SEQ ID NO:16)

TTAGATCCCCAACACATGGTGGNTAATCCTACATCCACATAATGTAACATGGTTGATNTGGCCGTTGTGATATACATGGCGG
CCCCTACGCCGTTGGCCTTCCTCTCTCTCTCTTCTCTATATCTCTTTCTTGATCTCTCTATAAAGCTCAAATAGCC
CAGCAAGCAAAATAATCCAAAAGAACAAGATAAGAAGAACCAAACTCGCAAAGAAACAAACAAAAAAAAAAAA
AAACGAATTAAAAAAAGAAGAATAAATCCCTTTTTAACACCTCATTCTCCGGCACTCAAAAGAGACCAA
AGAAGAAAACTTTAGCTCTCCTTTGTGTTTCTCTTTTCTTGTTGTTCCGACAATGGAGGAGAAGAAGTAGCA
GCTGGTTCATTCCAAAGGTTCTTGTTCTGTCTGTAATCTTAAGTCCTTGTAATAGTGAAGGGTATGTCTCTGTTATGGTG
GAGACCAAGAAAGATTGAAGAACATTTCTAAACAAGGAATTCGAGGTCCTCCTTATCATTTCTTCATCGGAAATGTTA
AAGAACTTGTTGAATGATGCTTAAAGCT

SEQUENCE LISTING

<160> NUMBER OF SEQ ID NOS: 16

<210> SEQ ID NO 1
<211> LENGTH: 1563
<212> TYPE: DNA
<213> ORGANISM: Arabidopsis thaliana
<220> FEATURE:
<223> OTHER INFORMATION: Oligonucleotide

<400> SEQUENCE: 1

```
atggaggaag aaagtagcag ctggttcatt ccaaaggttc ttgttctgtc tgtaatctta      60
agtcttgtaa tagtgaaggg tatgtctctg ttatggtgga gaccaagaaa gattgaagaa     120
catttctcta aacaaggaat tcgaggtcct ccttatcatt tcttcatcgg aaatgttaaa     180
gaacttgttg gaatgatgct taaagcttct tctcatccta tgcctttctc tcacaatatt     240
cttcctagag ttctctcttt ttaccatcac tggagaaaaa tctacggtgc tacatttctg     300
gtttggttcg gtccaacttt ccggttaacg gtagccgatc ctgatttgat cagagagatc     360
ttctctaagt ctgagttcta cgagaagaat gaagctcacc ctttggttaa acaacttgaa     420
ggcgatggac tacttagtct caaaggtgaa aaatgggctc atcatcgaaa aatcattagc     480
cctacttttc atatggagaa tcttaagttg cttgtaccag ttgtgttgaa gagtgtgact     540
gatatggtgg ataaatggtc cgataagtta tcagaaaacg gtgaagttga ggtagatgtc     600
tatgagtggt ttcagatttt gactgaagat gttattagta gaacagcttt tggaagtagc     660
tatgaagatg gtcgagcagt ttttcgactt caagctcaac aaatgcttct ttgtgctgaa     720
gcttttcaaa aagtcttcat tcctggctat agattttttc cgacaagagg gaatttgaag     780
tctcggaagt tagacaagga gataaggaag tcgttgttga agctgataga gcggcggaga     840
caaaacgcta tagatggaga aggggaagaa tgtaaggagc cggcggcgaa ggatttgttg     900
ggattaatga ttcaggcaaa gaatgtgacg gttcaggaca ttgtggagga gtgtaaaagc     960
tttttcttcg ccgggaaaca gacaacttct aatctgctga cgtggacgac catcttgcta    1020
tccatgcacc cggagtggca ggccaaagca cgtgatgagg tcctcagggt ctgcggctca    1080
cgtgatgtcc ctaccaagga ccatgtcgtt aagcttaaaa cgttgagtat gatcttgaac    1140
gagtctttaa ggttgtatcc accaatagta gctacgattc gacgcgctaa atcggatgtg    1200
aagctaggag ggtacaaaat cccatgtggc acggagcttc taatcccaat catagcggtc    1260
catcatgacc aagccatttg gggtaatgac gtgaacgaat tcaatccagc tcggtttgcg    1320
gatggagtgc cgcgtgctgc caaacacccc gttggcttca taccgtttgg cctcggagtt    1380
cgtacatgca ttggtcagaa tcttgctata cttcaggcca aattgacact cgctgtaatg    1440
atccaacgct tcaccttttca cttggctcct acttatcagc atgcacctac cgtccttatg    1500
```

```
ttgctttatc ctcaacatgg tgcaccaatc accttccgga gattgaccaa tcatgaggat    1560
tga                                                                 1563
```

<210> SEQ ID NO 2
<211> LENGTH: 520
<212> TYPE: PRT
<213> ORGANISM: Arabidopsis thaliana

<400> SEQUENCE: 2

```
Met Glu Glu Ser Ser Trp Phe Ile Pro Lys Val Leu Val Leu
 1               5                  10                  15

Ser Val Ile Leu Ser Leu Val Ile Val Lys Gly Met Ser Leu Leu Trp
            20                  25                  30

Trp Arg Pro Arg Lys Ile Glu His Phe Ser Lys Gln Gly Ile Arg
        35                  40                  45

Gly Pro Pro Tyr His Phe Phe Ile Gly Asn Val Lys Glu Leu Val Gly
    50                  55                  60

Met Met Leu Lys Ala Ser Ser His Pro Met Pro Phe Ser His Asn Ile
65                  70                  75                  80

Leu Pro Arg Val Leu Ser Phe Tyr His His Trp Arg Lys Ile Tyr Gly
                85                  90                  95

Ala Thr Phe Leu Val Trp Phe Gly Pro Thr Phe Arg Leu Thr Val Ala
            100                 105                 110

Asp Pro Asp Leu Ile Arg Glu Ile Phe Ser Lys Ser Glu Phe Tyr Glu
        115                 120                 125

Lys Asn Glu Ala His Pro Leu Val Lys Gln Leu Glu Gly Asp Gly Leu
    130                 135                 140

Leu Ser Leu Lys Gly Glu Lys Trp Ala His His Arg Lys Ile Ile Ser
145                 150                 155                 160

Pro Thr Phe His Met Glu Asn Leu Lys Leu Leu Val Pro Val Val Leu
                165                 170                 175

Lys Ser Val Thr Asp Met Val Asp Lys Trp Ser Asp Lys Leu Ser Glu
            180                 185                 190

Asn Gly Glu Val Glu Val Asp Val Tyr Glu Trp Phe Gln Ile Leu Thr
        195                 200                 205

Glu Asp Val Ile Ser Arg Thr Ala Phe Gly Ser Ser Tyr Glu Asp Gly
    210                 215                 220

Arg Ala Val Phe Arg Leu Gln Ala Gln Gln Met Leu Leu Cys Ala Glu
225                 230                 235                 240

Ala Phe Gln Lys Val Phe Ile Pro Gly Tyr Arg Phe Phe Pro Thr Arg
                245                 250                 255

Gly Asn Leu Lys Ser Arg Lys Leu Asp Lys Glu Ile Arg Lys Ser Leu
            260                 265                 270

Leu Lys Leu Ile Glu Arg Arg Gln Asn Ala Ile Asp Gly Glu Gly
        275                 280                 285

Glu Glu Cys Lys Glu Pro Ala Ala Lys Asp Leu Leu Gly Leu Met Ile
    290                 295                 300

Gln Ala Lys Asn Val Thr Val Gln Asp Ile Val Glu Glu Cys Lys Ser
305                 310                 315                 320

Phe Phe Phe Ala Gly Lys Gln Thr Thr Ser Asn Leu Leu Thr Trp Thr
                325                 330                 335

Thr Ile Leu Leu Ser Met His Pro Glu Trp Gln Ala Lys Ala Arg Asp
            340                 345                 350
```

```
Glu Val Leu Arg Val Cys Gly Ser Arg Asp Val Pro Thr Lys Asp His
        355                 360                 365
Val Val Lys Leu Lys Thr Leu Ser Met Ile Leu Asn Glu Ser Leu Arg
    370                 375                 380
Leu Tyr Pro Pro Ile Val Ala Thr Ile Arg Arg Ala Lys Ser Asp Val
385                 390                 395                 400
Lys Leu Gly Gly Tyr Lys Ile Pro Cys Gly Thr Glu Leu Leu Ile Pro
                405                 410                 415
Ile Ile Ala Val His His Asp Gln Ala Ile Trp Gly Asn Asp Val Asn
            420                 425                 430
Glu Phe Asn Pro Ala Arg Phe Ala Asp Gly Val Pro Arg Ala Ala Lys
        435                 440                 445
His Pro Val Gly Phe Ile Pro Phe Gly Leu Gly Val Arg Thr Cys Ile
    450                 455                 460
Gly Gln Asn Leu Ala Ile Leu Gln Ala Lys Leu Thr Leu Ala Val Met
465                 470                 475                 480
Ile Gln Arg Phe Thr Phe His Leu Ala Pro Thr Tyr Gln His Ala Pro
                485                 490                 495
Thr Val Leu Met Leu Leu Tyr Pro Gln His Gly Ala Pro Ile Thr Phe
        500                 505                 510
Arg Arg Leu Thr Asn His Glu Asp
        515                 520

<210> SEQ ID NO 3
<220> FEATURE:
<223> OTHER INFORMATION: Primer
<211> LENGTH:
<212> TYPE:
<213> ORGANISM:

<400> SEQUENCE: 3

000

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 4
ctgtcgtgga aagtgtgagg                                              20

<210> SEQ ID NO 5
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 5
gaaccttgac gcttgagg                                                18

<210> SEQ ID NO 6
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 6
```

-continued

| | |
|---|---|
| gctctctcga ggtcgacgg | 19 |

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7

| | |
|---|---|
| gcttgctgga ctatttgagc | 20 |

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 8

| | |
|---|---|
| ggttcaggac attgtggagg | 20 |

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 9

| | |
|---|---|
| ggatacaacc ttaaagactc g | 21 |

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 10

| | |
|---|---|
| gcaactcggt aacgacaggc | 20 |

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 11

| | |
|---|---|
| tcaagtagca aaatcacggc g | 21 |

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 12

| | |
|---|---|
| ctctttaatc cttggagatg gc | 22 |

<210> SEQ ID NO 13
<211> LENGTH: 25
<212> TYPE: DNA
<213> ORGANISM: Artificial Sequence -continued

```
<220> FEATURE:
<223> OTHER INFORMATION: Oligonucleotide primer

<400> SEQUENCE: 13
ggttgatcat cttctgctaa ttccc                                                25

<210> SEQ ID NO 14
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 14
gatctttgcc ggaaaacaat tggaggatgg t                                         31

<210> SEQ ID NO 15
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 15
cgacttgtca ttagaaagaa agagataaca gg                                        32

<210> SEQ ID NO 16
<211> LENGTH: 588
<212> TYPE: DNA
<213> ORGANISM: Arabidopsis thaliana
<220> FEATURE:
<221> NAME/KEY: misc_feature
<222> LOCATION: (1)...(588)
<223> OTHER INFORMATION: n = A,T,C or G

<400> SEQUENCE: 16
ttagatcccc aacatggtgg ntaatcctac atccacataa tgtaacatgg ttgatntggc          60
cgttgtgata tacatggcgg cccctacgcc gttggccttc ctctctctct ctttctctat         120
atctctttct tgatctctct ctataaaagc tcaaatagcc cagcaagcaa aataatccaa         180
aaagaaacca agataagaag aaacaaactc gcaaagaaac aaaaaggaaa aaaaaaaaa          240 aaacgaatta aaaaaagaag aaataaatcc tcctttttaa cacctcattc cctctttctc         300
cggcactcaa aagagaccaa agaagaaaac tttagctctc cttttttgtgt tttctctctt       360 ttctttgttg gtgttccgac aatggaggaa gaaagtagca gctggttcat tccaaaggtt        420
cttgttctgt ctgtaatctt aagtccttgt aatagtgaag ggtatgtctc tgttatggtg       480
gagaccaaga aagattgaag aacatttctc taaacaagga attcgaggtc ctccttatca       540
tttcttcatc ggaaatgtta aagaacttgt tgaatgatgc ttaaagct                     588
```

GENETICALLY MODIFIED PLANTS HAVING MODULATED BRASSINOSTEROID SIGNALING

RELATED APPLICATIONS

This application is a divisional application of U.S. application Ser. No. 09/527,073, filed on Mar. 16, 2000, now U.S. Pat. No. 6,534,313, which claims the benefit under Section 119(e)(1) of U.S. Provisional Patent Application Ser. No. 60/172,832, filed Dec. 20, 1999; U.S. Provisional Patent Application Ser. No. 60/170,931, filed Dec. 14, 1999; and U.S. Provisional Patent Application Ser. No. 60/124,570, filed Mar. 16, 1999.

FIELD OF THE INVENTION

The present invention relates generally to plant growth and development and more specifically to methods of modifying brassinolide activity in plants by modulating cytochome P450 activity.

BACKGROUND OF THE INVENTION

A plant is considered healthy when it can carry out its physiological functions, such as cell division, differentiation, development, photosynthesis, absorption and translocation of water and nutrients from the soil, metabolism, reproduction, and storage of food supplies, without disruption. When plant functions are disturbed by pathogens or insects, the plants become diseased or destroyed. Disease can be defined as the malfunctioning of plant host cells and tissues caused by continuous irritation by a pathogenic agent or insect. A disease involves abnormal changes in the form, physiology, or behavior of the plant.

Representative insects or pests that attack plants include Coleoptera and Lepidoptera such as western corn root worm (*Diabrotica virgifera virgifera*), northern corn root worm (*Diabrotica longicornis barberi*), southern corn rootworm (*Diabrotica undecimpunctata howardi*), cotton bollworm, European corn borer, corn root webworm, pink bollworm and tobacco budworm. The transgenic plants are preferably monocotyledoneous or dicotyledoneous plants. Plant pathogenic bacteria also cause a variety of plant disease symptoms. About 80 species of bacteria (e.g., *Pseudomonas viridiflava, Xanthomonas campestris* pv. *asclepiadas, Xyella fastidiosa, Acidovorax albilineans,* and *Acidovorax avenae* sspl *citrulli*) cause disease in plants, including fruit rot, galls, wilts, blight, and leaf spots. As bacteria multiply quickly, controlling them early in the disease process is critical. Copper and streptomycin compounds are the only chemical compounds currently available for the control of bacterial diseases.

Genetic engineering of plants, which entails the isolation and manipulation of genetic material, e.g., DNA or RNA, and the subsequent introduction of that material into a plant or plant cells, has changed plant breeding and agriculture considerably over recent years. Increased crop food values, higher yields, feed value, reduced production costs, pest resistance, stress tolerance, drought resistance, the production of pharmaceuticals, chemicals and biological molecules as well as other beneficial traits are all potentially achievable through genetic engineering techniques. Genetic engineering techniques supplying the genes involved in pathogen resistance have the potential to substantially affect crop production.

Traditionally, the control of plant stature has been through the process of selective breeding. Often dwarf plants are chosen for their ornamental value or their improved ability to survive under mechanical stress, such as high wind. However, this breeding process can take many years. An alternative way to rapidly create dwarf plants is by the exogenous application of certain organic compounds, such as the gibberellin biosynthesis inhibitor, uniconazole. However, these compounds are expensive and must be applied throughout the plant life cycle.

Light also has an important role in plant development, both for photosynthesis and as a developmental cue. A variety of photoreceptors respond to the quality, quantity, direction and duration of the light environment. In *Arabidopsis* there are five red/far-red absorbing phytochromes (phyA-phyE), two blue/UVA absorbing cryptochromes (cry1 and 2) and the less understood UVB photoreceptors. All affect gross morphological changes in seedling development as they deetiolate, making the transition from growth in the dark to growth in the light (C. Fankhauser and J. Chory, *Annu Rev Cell Dev Biol* 13:203–29, 1997). Genetic analysis demonstrates a complex web of interactions between these photoreceptor signaling pathways (Casal and Mazzella, *Plant Physiol* 118:19–25, 1998; M. M. Neff and J. Chory, *Plant Physiol.* 118:27–35, 1998; L. Hennig et al., *Planta* 208:257–263, 1999; G. Lasceve et al., *Plant Physiol* 120:605–614, 1999). There is also a distinct class of photoreceptors, the phototropins (e.g. NPH1), which effect the directional growth of seedlings (E. Liscum and W. R. Briggs, *Plant Cell* 7:473–485, 1995; E. Huala et al., *Science* 278:2120–2123, 1997; J. M. Christie et al., *Science* 282: 1698–701, 1998), a process that can be modified by the activity of phytochromes (B. M. Parks et al., *Plant Physiol.* 110:155–162, 1996).

Plant hormones can also contribute to photomorphogenic responses. Some photomorphogenetic mutants resemble mutants involved in phytohormone biosynthesis or sensing. For example, the GA signaling mutant spindly resembles plants with mutations in phyB, which have long stems, pale leaves and early flowering. This phenotype can also be mimicked in wild type plants by the application of $GA_3$ (S. E. Jacobsen and N. E. Olszewski, *Plant Cell* 5:887–896, 1993). Genetic analysis of GA and phytochrome mutants points to interactions between these two signal transduction systems for certain responses (J. Chory, *Plant Cell* 9:1225–34, 1997). However, other responses, such as flowering, are likely to be independently controlled by both systems (M. A. Blázquez and D. Weigel, *Plant Phys* 120: 1025–32, 1999).

Gibberellins are not the only hormones that are involved in light signaling. Auxins clearly have some role in photomorphogenesis. For example, auxin transport is affected in a light dependent manner (P. J. Jensen et al., *Plant Physiol* 116:455–462, 1998). Genetic analysis also points towards a role for auxin in light signal transduction. The shy2 mutation, identified in a suppressor screen for mutants with reduced levels of all phytochromes (Kim et al.[In Process Citation]. *Plant J* 15:61–68) or in a null mutant of phyB (J. W. Reed et al., *Genetics* 148:1295–1310, 1998), resides in the auxin induced gene IAA3 (Q. Tian and J. W. Reed, *Development* 126:711–21, 1999). A third example of the interplay between photomorphogenesis and phytohormones is that many brassinosteroid mutants have been identified in genetic screens for plants that can undergo deetiolation in the absence of a light cue (for review see (J. Li and J. Chory, *Exp Bot* 50:275–282, 1999)). When these mutants are grown in the dark, their seedlings have short hypocotyls with cotyledons that begin to develop as if growing in the light. As adults, these mutants are dwarfs with dark-green, epinastic leaves and short stems and petioles. They are slow growing with delayed senescence. Each of these adult phenotypes is essentially the opposite of mutants lacking phytochrome B (for review see (Chory, 1997, supra)).

Genetic screens for loss-of-function mutations have led to the identification of many loci thought to be involved in photomorphogenesis (Fankhauser and Chory, supra). However, these screens may miss important components of light signal transduction that are either redundant members of a gene family or are essential for survival. The role of such genes may only be identified in gain-of-function mutant screens. One method for targeting gain-of-function mutations is through extragenic suppressor analysis (G. Prelich, *Trends Genet* 15:261–6, 1999).

This approach has been used successfully in *Arabidopsis* to identify dominant or semidominant mutants involved in light signal transduction (A. Pepper and J. Chory, *Genetics* 145:1125–37, 1997; Kim et al., supra; Reed et al., 1998, supra). However, positional cloning of dominant or semidominant extragenic suppressors can be difficult and time consuming if they do not have a phenotype in a wild type background. shy2 is the only dominant, extragenic suppressor mutation cloned by map based methods in *Arabidopsis* and has a striking phenotype in a wild type background (Tian and Reed, supra).

A gene tagging approach has been used to circumvent the difficulties of map-based cloning of mutations in *Arabidopsis*. In this approach, mutants are generated by transformation with *Agrobacterium* mediated transfer-DNA (T-DNA). Since the T-DNA sequence is known, mutations that are tagged by the transgene can be easily identified and cloned (F. J. Behringer and J. I. Medford, *Plant Molecular Biology Reporter* 10:190–198, 1992; Y. -G. Liu et al., *Plant J.* 8:457–463, 1995.

However, these mutations are primarily caused by the loss of gene function. Thus, the amount of information that can be gleaned from their identification is limited. A modification of T-DNA tagging has been developed that specifically targets gain-of-function mutations. In this approach, multimerized copies of enhancer elements from the cauliflower mosaic virus (CaMV) 35S promoter are incorporated near the right border of a T-DNA. When these enhancers are inserted near a gene, its transcription may be enhanced; resulting in a dominant, tagged mutation (R. Walden et al., *Plant Mol Biol* 26:1521–8, 1994).

SUMMARY OF THE INVENTION

The present invention is based on the discovery that bas1 gene in *Arabidopsis thalia* encodes a cytochrome P450 (CYP72B1), which has a role in brassinosteroid signaling or synthesis. Overexpression of the bas1 gene in plants causes a dark green, dwarf phenotype which mimics plants that have low levels of the plant hormone, brassinolide. Overexpression of the bas1 gene also increases resistance to insects in plants. Biochemical analysis shows that CYP72B1 is a C-26 hydroxylase of brassinolide, targeting it for inactivation. Transgenic plants engineered to overexpress bas1 gene have severely reduced levels of brassinolide and some brassinosteroid precursors. Overexpression of the bas1 gene in Tobacco (*Nicotiana tabacum*) confers a similar phenotype, indicating that this gene is functionally active in a divergent plant family. Based on these observations, the present invention provides plants genetically modified with bas1 gene, or functional homologues or functional fragments thereof, wherein such plants exhibit modulated brassinosteroid signaling or synthesis as compared to wild-type plants.

Accordingly, in a first embodiment, the invention provides a BAS1 polypeptide that modulates brassinolide activity in plants. Also included are polynucleotides encoding BAS1 and antibodies that bind to BAS1.

In another embodiment, the invention provides a genetically modified plant comprising at least one exogenous nucleic acid sequence encoding a cytochrome P450, e.g., BAS1 polypeptide or functional equivalent, in its genome or at least one regulatory sequence that modifies expression of endogenous cytochrome P450, e.g., bas1 gene and which is characterized as having modulated brassinolide activity compared to a wild-type plant. Such genetically modified plants may exhibit dwarfism with dark-green leaves in adult plants.

In another embodiment, the invention provides a method for genetically modifying a plant cell such that a plant, produced from the cell, is characterized as having modulated brassinolide activity as compared with a wild-type plant. The invention method for modifying a plant cell comprises introducing at least one exogenous cytochrome P450, e.g., bas1 polynucleotide, into a plant cell to obtain a transformed plant cell, and growing the transformed plant cell under conditions that permit expression of cytochrome P450, e.g., bas1 gene product, thereby producing a plant having modulated brassinolide activity.

In another embodiment, the invention provides a method of producing a genetically modified plant characterized as having dwarf adult stature with dark green foliage, by contacting a plant cell with a vector containing an exogenous nucleic acid sequence comprising at least one structural gene encoding a cytochrome P450, e.g., BAS1 polypeptide, the gene being operably associated with a regulatory sequence that causes overexpression of the gene, to obtain a transformed plant cell, producing a plant from the transformed plant cell; and selecting a plant exhibiting dwarf adult stature with dark-green foliage.

In another embodiment, the invention provides a genetically modified plant having a transgene increasing expression of bas1 gene, chromosomally integrated into the genome of the plant.

In another embodiment, the invention provides a method of producing a genetically modified plant characterized as being hyperresponsive to brassinolide, by contacting a plant cell with a vector containing an exogenous nucleic acid sequence encoding a product that disrupts or interferes with expression of cytochrome P450, e.g., BAS1 polypeptide, which nucleic acid is operably associated with a promoter, to obtain a transformed plant cell, producing a plant from the transformed plant cell; and selecting a plant exhibiting hyperresponsiveness to brassinolide in a light-dependent manner.

In another embodiment, the invention provides a method for genetically modifying a plant cell such that a plant, produced from the cell, is characterized as having modulated ecdysteroid activity as compared with a wild-type plant. In this embodiment, the invention method comprises introducing at least one exogenous cytochrome P450, e.g., bas1 polynucleotide, into a plant cell to obtain a transformed plant cell; and growing the transformed plant cell under conditions the permit expression of the cytochrome P450, e.g., bas1 gene product, thereby producing a plant having modulated ecdysteroid activity.

In another embodiment, the invention provides a method of producing a genetically modified plant characterized as having increased disease or insect resistance as compared to a corresponding wild-type plant. The method includes contacting plant cells with nucleic acid encoding an BAS1 polypeptide or functional fragment thereof, operatively associated with an expression control sequence, to obtain transformed plant cells; producing plants from the transformed plant cells; and selecting a plant exhibiting increased disease or insect resistance. A method for genetically modifying a plant cell such that a plant produced from the cell is characterized as having increased disease or insect as compared with a wild-type plant is also provided. The method includes introducing an isolated polynucleotide encoding a BAS1 polypeptide into a plant cell to obtain a transformed plant cell, and growing the transformed plant cell under conditions which permit expression of BAS1 polynucleotide thereby producing a plant having increased disease or resistance.

In a further embodiment, a method is provided for producing a genetically modified plant characterized as having increased disease or insect resistance as compared to the corresponding wild type plant by contacting a susceptible plant with a BAS1 promoter-inducing amount of an agent necessary to elevate BAS1 gene expression above BAS1 expression in a plant not contacted with the agent. For example, the agent may be a transcription factor or a chemical agent, such as dexamethasone (DEX).

A method is also provided for producing genetically transformed, disease or insect resistant plants, by introducing into the genome of a plant cell, to obtain a transformed plant cell, a nucleic acid sequence having an expression control sequence operably linked to a polynucleotide encoding a BAS1 polypeptide. The invention also provides plants, plant tissue, and seeds produced by plants produced by the methods of the invention.

In yet another embodiment, a method is provided for identifying novel disease or insect resistance genes or genes capable of inducing reduced stature in plants by probing a nucleic acid library with at least a fragment of a polynucleotide encoding BAS1, and selecting those clones that hybridize with the fragment.

In another embodiment, the invention provides an isolated nucleic acid sequence comprising a non-coding regulatory sequence isolated upstream from a bas1 gene, wherein said nucleic acid sequence contains at least one restriction site for cloning a heterologous nucleic acid sequence of interest. An exemplary bas1 regulatory sequence is shown in FIG. 1C (SEQ ID NO:16). The invention also provides a nucleic acid construct comprising, reading from the 5' to 3' direction, a 5' non-coding sequence isolated from bas1 gene and a nucleic acid sequence encoding a structural gene, wherein said nucleic acid sequence is heterologous to said 5' non-coding sequence. The construct is useful for the production of transgenic plants which express a gene of interest in a tissue-specific manner, for example.

BRIEF DESCRIPTION OF THE DRAWINGS

FIGS. 1A and 1B show the nucleotide and deduced amino acid sequences of BAS1 (SEQ ID NO:1 and 2, respectively). (See also GenEMBL accession number AC003105 which encodes the full length EST cDNA T04442, which is hereby incorporated herein by reference). FIG. 1C shows the promoter sequence for bas1 (SEQ ID NO:16).

FIG. 3A shows the dose response in hypocotyls of light grown seedlings and FIG. 3B shows the dose response in hypocotyls of dark-grown seedlings. FIG. 3C shows the dose response of cotyledon petioles after 12 days of growth in white light. Col-O=closed circles; phyB-4 =open diamonds; bas1-DphyB-4 =open circles; BAS1 antisense line=closed diamonds; and det2-1=open triangles. Error bars represent one standard error from the mean. When no error bars are visible, they are smaller than the symbols.

FIG. 4A shows the response to white light; FIG. 4B shows the response to far-red-light; FIG. 4C shows the response to blue light; and FIG. 4D shows the response to red-light. The lines tested are Col-O (closed circles), phyB-4 (open diamonds), bas1-DphyB-4 (open circles), BAS1 antisense line (closed diamonds) and det2-1 (open triangles). Error bars represent one standard error from the mean. When no error bars are visible, they are smaller than the symbols.

FIG. 5A compares phyB-4phyA-201 mutants segregating the bas1-D mutation (hatched bars) with the control lines (open bars) in 15 $\mu g Em^{-2} s^{-1}$ of continuous far-red light for six days. FIG. 5B compares the phyB-4cry1 mutants segregating the bas1-D mutation (hatched bars) with control lines (open bars) in 20 $\mu Em^{-2} s^{-1}$ of continuous blue light for six days. Error bars represent one standard error from the mean.

DETAILED DESCRIPTION

Figure 2:
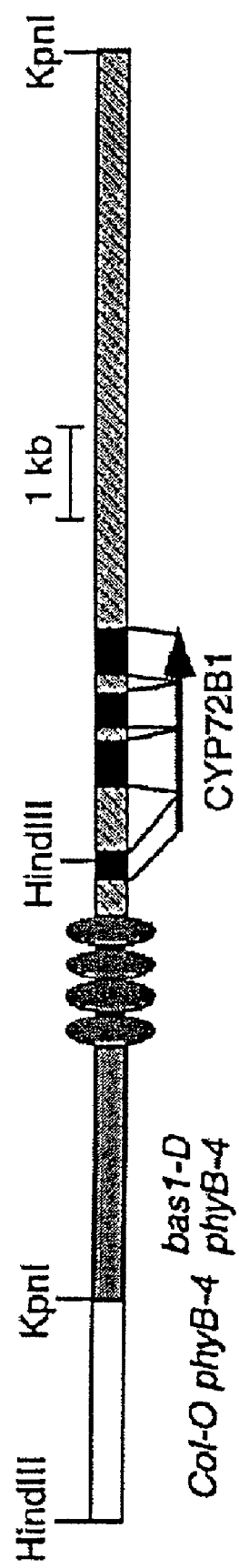
FIG. 2 is a schematic diagram showing the insertion of CaMV 35S enhancer elements into genomic DNA in pBlue-Script® plasmid used for plasmid rescue. White represents part of the T-DNA; ovals represent the enhancer elements, hatches represent plant genomic DNA.

The present invention is based on the seminal discovery that a cytochrome P450, when expressed at increased levels in a plant, as compared to a wild-type plant, is effective in providing reduced stature and/or insect resistance to the plant. While not wanting to be bound by a particular theory, it is believed that P450, e.g., CYP72B1 catalyzes the C26-hydroxylation of brassinosteroids and therefore can likely catalyze the C26-hydroxylation of ecdysone, thus preventing predators from undergoing molting after feeding on plants expressing high levels of the cytochrome P450. An illustrative cytochrome P450 is provided herein however, the invention is understood to include any P450 having the activity as described for this illustrative species.

The exemplary cytochrome described herein is a substantially pure cytochrome P450 (CYP72B1), BAS1, the expression product of bas1 gene in *Arabidopsis thalia*. It should be understood that BAS1 is provide for exemplary purposes and the invention is not to be construed as limited only to this cytochrome P450. Overexpression of bas1 in transgenic plants causes such plants to exhibit decreased stature accompanied by darker green foliage compared to their wild-type counterparts. The proteins encoded by the nucleic acid molecules according to the invention comprise preferably domains characteristic for cytochrome P450 proteins (see, for example, Nebert and Gonzalez, Ann. Rev. Biochem. 56 (1987), 945–993). Furthermore, it is preferred that the proteins encoded by the nucleic acid molecules according to the invention contain domains characteristic for steroid hydroxylases, namely steroid binding domains. Preferably the proteins have the enzymatic activity of a steroid hydroxylase.

In a first embodiment, the present invention provides an exemplary cytochrome P450 useful in the methods of the invention. A substantially pure BAS1 polypeptid is exemplified by the amino acid sequence shown in FIG. 1 (SEQ ID NO:2). BAS1 polypeptide is characterized as having a predicted molecular weight of approximately 56 kD as determined by SDS-PAGE, being a cytochrome P450 (CYP72B1), being a dominant suppressor of phyB-4, and modulating brassinolide activity in plants. Also included are biologically active fragments or homologues of BAS1 polypeptide. Such fragments can be identified, for example, by the methods provided in the Examples herein.

The term "BAS1 polypeptide" as used herein means the BAS1 polypeptide having the amino acid sequence of SEQ ID NO:2, as well as functional fragments thereof, along with other homologous plant cytochrome P450s, such as CYP72A from *Catharanthus roseus* (Madagascar periwinkle), which has about 42% sequence identity with BAS1 at the amino acid level and the CYP72 chibi2 from *Arabidopsis*.

The term "substantially pure" as used herein refers to BAS1 polypeptide that is substantially free of other proteins, lipids, carbohydrates or other materials with which it is naturally associated. One skilled in the art can purify BAS1 using standard techniques for protein purification. The substantially pure polypeptide will yield a single major band of about 56 kD on a denaturing polyacrylamide gel, such as SDS-PAGE. The purity of the BAS1 polypeptide can also be determined by amino-terminal amino acid sequence analysis.

The invention includes functional BAS1 polypeptide, and functional fragments thereof. As used herein, the term "functional polypeptide" refers to a polypeptide which possesses biological function or activity which is identified through a functional assay (e.g., brassinolide activity) and which is associated with a particular biologic, morphologic, or phenotypic alteration in the cell. For example, overexpression of BAS1 polypeptide results in modulation of brassinolide activity, characterized by one or more of the following: hypersensitivity to far-red light in a PHYA background and lack of responsiveness in a phyA null background, etiolation with hypocotyls of near wild-type length in dark grown seedlings, and dwarfism with dark-green leaves in adult plants.

The term "functional fragments of BAS1 polypeptide", refers to all fragments of BAS1 that retain BAS1 activity, e.g., being a dominant suppressor of phyB-4, being a cytochrome P450, modulating brassinolide activity in plants. Biologically functional fragments, for example, can vary in size from a polypeptide fragment as small as an epitope capable of binding an antibody molecule to a large polypeptide capable of participating in the characteristic induction or programming of phenotypic changes within a cell. Functional fragments of BAS1 include antigenic fragments.

The brassinolide modulating activity of BAS1 can be utilized in bioassays to identify biologically active fragments of BAS1 polypeptide or related polypeptides. For example, BAS1 may modulate brassinolide activity in diverse tissues, or in a tissue specific manner; therefore an assay can be performed to detect BAS1 brassinolide activity. Inhibitors of BAS1, such as BAS1 antisense nucleic acids, could be used to cause loss of function of BAS1 resulting in, for example, hypocotyls that are slightly longer than the wild type in dark growth, and have a reduced responsiveness to white, far-red and blue light, compared with wild type plants.

The polypeptides of the invention also include dominant negative forms of the BAS1 polypeptide that do not have the biological activity of BAS1. A "dominant negative form" of BAS1 is a polypeptide that is structurally similar to BAS1 but does not have wild-type BAS1 function. For example, a dominant-negative BAS1 polypeptide may interfere with wild-type BAS1 function by binding to, or otherwise sequestering, regulating agents, such as upstream or downstream components, that normally interact functionally with the BAS1 polypeptide.

Minor modifications of the BAS1 primary amino acid sequence may result in proteins that have substantially equivalent activity to the BAS1 polypeptide described herein in SEQ ID NO:2 (FIG. 1). Such modifications may be deliberate, as by site-directed mutagenesis, or may be spontaneous. All of the polypeptides produced by these modifications are included herein, as long as the biological activity of BAS1 is present, e.g., modification of brassinolide or ecdysteroid synthesis and/or signaling activity is present. Further, deletion of one or more amino acids can also result in a modification of the structure of the resultant molecule without significantly altering its activity. This can lead to the development of a smaller active molecule that could have broader utility. For example, it may be possible to remove amino or carboxy terminal amino acids not required for BAS1 activity.

BAS1 polypeptide includes amino acid sequences substantially the same as the sequence set forth in SEQ ID NO:2. The invention includes polypeptides having substantially the same sequence of amino acids as the amino acid sequence set forth in SEQ ID NO:2, functional fragments thereof, and amino acid sequences that are substantially identical to SEQ ID NO:2. By "substantially the same" or "substantially identical" is meant a polypeptide or nucleic acid exhibiting at least 80%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides. BAS1 homologs can be identified as having a % homology with BAS1 within these ranges.

Functional fragments include those fragments of BAS1 that retain the function or activity of BAS1, such as the ability to modulate brassinolide synthesis or signaling. One of skill in the art can screen for the functionality of a fragment by using the examples provided herein, where full-length BAS1 is described. It is also envisioned that fragments of BAS1 that inhibit or promote brassinolide synthesis or signaling can be identified in a similar manner.

By "substantially identical" is also meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed, (e.g., as described herein). Preferably, such a sequence is at least 85%, more preferably 100% identical at the amino acid level to SEQ ID NO:2.

Homology is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications.

By a "substantially pure polypeptide" is meant an BAS1 polypeptide that has been separated from components that naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, BAS1 polypeptide. A substantially pure BAS1 polypeptide may be obtained, for example, by extraction from a natural source (e.g., a plant cell); by expression of a recombinant nucleic acid encoding a BAS1 polypeptide; or by chemically synthesizing the protein. Purity can be measured by any appropriate method, e.g., those described in column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms, but synthesized in *E. coli* or other prokaryotes.

The invention provides polynucleotides encoding the BAS1 protein. These polynucleotides include DNA, cDNA and RNA sequences which encode BAS1. It is understood that all polynucleotides encoding BAS1 are also included herein, as long as they encode a polypeptide with BAS1 activity. Such polynucleotides include naturally occurring, synthetic, and intentionally manipulated polynucleotides. For example, bas1 polynucleotide may be subjected to site-directed mutagenesis. The polynucleotide sequence encoding BAS1 also includes antisense sequences, sequences encoding dominant negative forms of BAS1, and sequences encoding BAS1 fragments or peptides. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of BAS1 polypeptide encoded by the nucleotide sequence is functionally unchanged.

Specifically disclosed herein is a polynucleotide sequence containing the bas1 gene. Preferably, the bas1 nucleotide sequence is SEQ ID NO:1. The term "polynucleotide" or "nucleic acid sequence" refers to a polymeric form of nucleotides at least 10 bases in length. By "isolated polynucleotide" or "purified polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote; or which exists as a separate molecule (e.g. a cDNA) independent of other sequences. The nucleotides of the invention can be ribonucleotides, deoxyribonucleotides, or modified forms of either nucleotide. The term includes single and double forms of DNA. It also includes a recombinant DNA that is part of a hybrid gene encoding additional polypeptide sequence.

The invention also provides an isolated polynucleotide sequence encoding a polypeptide having the amino acid sequence of SEQ ID NO:2. The bas1 transcript contains a single, long open reading frame that encodes an approximately 510-amino acid protein.

The polynucleotide encoding BAS1 includes the nucleotide sequence in FIG. 1 (SEQ ID NO:1), as well as nucleic acid sequences complementary to that sequence. A complementary sequence may include an antisense nucleotide. When the sequence is RNA, the deoxyribonucleotides A, G, C, and T of FIG. 1 are replaced by ribonucleotides A, G, C, and U, respectively. Also included in the invention are fragments ("probes") of the above-described nucleic acid sequences that are at least 15 bases in length, which is sufficient length to permit the probe to selectively hybridize to DNA that encodes the protein of FIG. 1 (SEQ ID NO:2). "Selective hybridization" as used herein refers to hybridization under moderately stringent or highly stringent physiological conditions (See, for example, the techniques described in Maniatis et al., *Molecular Cloning A Laboratory Manual*, Cold Spring Harbor Laboratory, N.Y., 1989, incorporated herein by reference), which distinguishes related from unrelated bas1 nucleotide sequences.

Specifically disclosed herein is a cDNA sequence for the bas1 gene. FIG. 1 shows the complete cDNA and deduced protein sequences (SEQ ID NO:1 and 2, respectively).

A "substantially identical" nucleic acid sequence codes for a substantially identical amino acid sequence as defined above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

A polynucleotide sequence encoding a BAS1 polypeptide of the invention includes nucleotide sequences encoding the disclosed sequence (e.g., SEQ ID NO:2) and conservative variations thereof. The term "conservative variation" as used herein denotes the replacement of an amino acid residue by another, biologically similar residue. Examples of conservative variations include the substitution of one hydrophobic residue, such as isoleucine, valine, leucine or methionine, for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences encoding BAS1 can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the bas1 polynucleotide sequences may be inserted into an expression vector. The term "expression vector" refers to a plasmid, virus or other vehicle known in the art that has been manipulated by insertion or incorporation of the BAS1-encoding genetic sequences. A polynucleotide sequence that encode BAS1 can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequence" refers to a nucleic acid sequence that regulates the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, a splicing signal for introns or maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or expression that is inducible by external signals or agents. Such elements may be located in the 5' or 3' regions of the gene. Both constitutive and inducible promoters, are included in the invention (see e.g., Bitter et al., 1987, *Methods in Enzymology* 153:516–544). The expression of structural genes employed in the present invention may be driven by a number of promoters. Although the endogenous promoter of a structural gene of interest may be utilized for transcriptional regulation of the gene, preferably, the promoter is a foreign regulatory sequence. For plant expression vectors, suitable viral promoters include the 35S RNA and 19S RNA promoters of CaMV (Brisson, et al, *Nature,* 310:511, 1984; Odell, et al., *Nature,* 313:810, 1985); the full-length transcript promoter from Figwort Mosaic Virus (FMV) (Gowda, et al, *J Cell Biochem.,* 13D:301, 1989) and the coat protein promoter of TMV (Takamatsu, et al., *EMBO J* 6:307, 1987). Alternatively, plant promoters such as the light-inducible promoter from the small subunit of ribulose bis-phosphate carboxylase (ssRUBISCO) (Coruzzi, et al., *EMBO J,* 3:1671, 1984; Broglie, et al., *Science,* 224:838, 1984); mannopine synthase promoter (Velten, et al., *EMBO J.,* 3:2723, 1984), nopaline synthase (NOS) and octopine synthase (OCS) promoters (carried on tumor-inducing plasmids of *Agrobacterium tumefaciens* and have plant activity); ethylene inducible promoter whose level of activity is increased in response to treatment with ethylene or an equivalent compound such as propylene; heat shock promoters, e.g., soybean hsp17.5-E or hsp17.3-B (Gurley, et al., *Mol. Cell. Biol.,* 6:559, 1986; Severin, et al., *Plant Mol Biol.,* 15:827, 1990); or ethanol-inducible promoters (Caddick et al., *Nature Biotech.,* 16:177, 1998) may be used.

Promoters useful in the invention include both constitutive and inducible natural promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter, which is activated by copper ions (Mett, et al., *Proc. Natl. Acad. Sci., U.S.A.,* 90:4567, 1993); In2-1 and In2-2 regulator sequences, which are activated by substituted benzene-sulfonamides, e.g., herbicide safeners (Hershey, et al., *Plant Mol. Biol.,* 17:679, 1991); the GRE regulatory sequences, which are induced by glucocorticoids (Schena, et al., *Proc. Natl. Acad. Sci., U.S.A.,* 88:10421, 1991); and ethanol-inducible promoters (Caddick et al., supra). Other promoters (both constitutive and inducible) and enhancers will be known to those of skill in the art.

The particular promoter selected should be capable of causing sufficient expression to result in the overexpression of the structural gene product, e.g., BAS1, to decrease brassinolide synthesis or signaling. Decreased brassinolide synthesis or signaling is characterized by hyperresponsiveness to brassinolide in a light-dependent manner, the presence of hypocotyls that are longer than the wild type, and reduced sensitivity to a variety of light conditions compared to wild type plants. The promoters used in the vector constructs of the present invention may be modified, if desired, to affect their control characteristics. In a preferred approach, multimerized copies of enhancer elements from the cauliflower mosaic virus (CaMV) 35S promoter are incorporated near (e.g., within 381 nucleotides) 5' to the start of the bas1 gene. When these enhancers are inserted near a gene, its transcription can be enhanced.

Tissue specific promoters may also be utilized in the present invention. As used herein, the term "tissue-specific promoter" means a DNA sequence that serves as a promoter, i.e., regulates expression of a selected DNA sequence operably linked to the promoter. A tissue-specific promoter effects expression of the selected DNA sequence in specific cells, e.g., in the root or in the shoot of a plant. The term also covers so-called "leaky" promoters, which regulate expression of a selected DNA primarily in one tissue, but cause expression in other tissues as well. Such promoters also may include additional DNA sequences that are necessary for expression, such as introns and enhancer sequences. An example of a tissue specific promoter is the HHA promoter expressed in shoot meristems (Atanassova, et al., *Plant J,* 2:291, 1992). Other tissue specific promoters useful in transgenic plants, including the cdc2a promoter and cyc07 promoter, will be known to those of skill in the art. (See for example, Ito, et al., *Plant Mol. Biol.*, 24:863, 1994; Martinez, et al., *Proc. Natl. Acad. Sci. USA*, 89:7360, 1992; Medford, et al., *Plant Cell*, 3:359, 1991; Terada, et al., *Plant Journal*, 3:241, 1993; Wissenbach, et al., *Plant Journal*, 4:411, 1993). Examples of tissue specific promoters active in floral meristems are the promoters of the apetala 3 and apetala 1 genes which are described in Jack et al., *Cell*, 76:703, 1994 and Hempel et al., *Development*, 124:3845, 1997. In addition, a meristem-specific promoter from the UFO gene (U.S. Pat. No. 5,880,330) may be useful in the practice of the inventors.

In another embodiment, the invention provides an isolated nucleic acid sequence comprising a non-coding regulatory sequence isolated upstream from a bas1 gene, wherein said nucleic acid sequence contains at least one restriction site for cloning a heterologous nucleic acid sequence of interest. An exemplary bas1 regulatory sequence is shown in FIG. 1C (SEQ ID NO:16). The invention also provides a nucleic acid construct comprising, reading from the 5' to 3' direction, a 5' non-coding sequence isolated from bas1 gene and a nucleic acid sequence encoding a structural gene, wherein said nucleic acid sequence is heterologous to said 5' non-coding sequence. The construct is useful for the production of transgenic plants which express a gene of interest in a tissue-specific manner, for example.

Optionally, a selectable marker may be associated with the heterologous nucleic acid sequence, i.e., the structural gene operably linked to a promoter. As used herein, the term "marker" refers to a gene encoding a trait or a phenotype that permits the selection of, or the screening for, a plant or plant cell containing the marker. The marker gene may be an antibiotic resistance gene that allows the appropriate antibiotic to be used to select for transformed cells from among cells that are not transformed, or the marker gene may be a herbicide resistance gene. Examples of suitable selectable markers include adenosine deaminase, dihydrofolate reductase, hygromycin-B-phosphotransferase, thymidine kinase, xanthine-guanine phospho-ribosyltransferase, glyphosphate and glufosinate resistance and amino-glycoside 3'-O-phosphotransferase II (kanamycin, neomycin and G418 resistance). Other suitable markers will be known to those of skill in the art.

Vector(s) employed in the present invention for transformation of a plant cell to modulate brassinolide synthesis or signaling comprise a nucleic acid sequence comprising at least one structural gene encoding a protein (e.g., BAS1) that modulates brassinolide synthesis or signaling, operably associated with a promoter. To commence a transformation process in accordance with the present invention, it is first necessary to construct a suitable vector and properly introduce it into the plant cell. The details of the construction of vectors suitable for use herein are known to those skilled in the art of plant genetic engineering. In the present invention, preferably the gene encoding a protein that modulates brassinolide synthesis or signaling is the bas1 gene. The bas1 gene may be utilized alone or in combination with another structural gene, such as another gene which encodes a protein important in brassinolide synthesis and/or signaling. Examples of such genes include bin1 and other examples of CYP72 in *Arabidopsis*, such as chibi2, and the like, and combinations thereof.

For example, the heterologous nucleic acid sequences utilized in the present invention can be introduced into plant cells using Ti plasmids, root-inducing (Ri) plasmids, and plant virus vectors. (For reviews of such techniques see, for example, Weissbach & Weissbach, *Methods for Plant Molecular Biology*, Academic Press, NY, Section VIII, pp. 421–463, 1998; Grierson & Corey, *Plant Molecular Biology*, 2d Ed., Blackie, London, Ch. 7–9, 1998; and Horsch et al., *Science*, 227:1229, 1985, is of which is incorporated herein by reference).

One of skill in the art will be able to select an appropriate vector for introducing the heterologous nucleic acid sequence in a relatively intact state. Thus, any vector which will produce a plant carrying the introduced DNA sequence should be sufficient. Even a naked piece of DNA would be expected to be able to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, *Methods of Enzymology, Vol. 153*, 1987, Wu and Grossman, Eds., Academic Press, incorporated herein by reference) and as disclosed in the Examples herein that illustrate the invention. As used herein, the term "transformation" means alteration of the genotype of a host plant by the introduction of a heterologous nucleic acid sequence. "Transformation" refers to the insertion of an exogenous polynucleotide into a host cell, irrespective of the method used for the insertion, for example, direct uptake, transduction, bombardment or electroporation. The exogenous polynucleotide may be maintained as a non-integrated vector, for example, a plasmid, or alternatively, may be integrated into the host genome.

One approach, known as direct transformation, induces uptake and integration of plasmid or linearized DNA in the genome of plant protoplasts, i.e., single cells stripped of cell wall material (Lorz et al., *Mol. Genet.* 199:178–182, 1985). Another approach involves the transfer of exogenous bacteriophage or plasmid DNA into germinating pollen grains to modify plant properties. As the pollen tube emerges from the mature pollen grain, cell wall material is deposited behind the growing tip.

A third approach relies on infection by *Agrobacterium* bacterium, which inserts sequences of a plasmid, known as the Ti-plasmid, into the genome of plant cells (Chilton et al., *Cell* 11:263:271, 1977). A heterologous nucleic acid sequence can be introduced into a plant cell utilizing *Agrobacterium tumefaciens* containing the Ti plasmid. In using an *A. tumefaciens* culture as a transformation vehicle, it is most advantageous to use a non-oncogenic strain of the *Agrobacterium* as the vector carrier so that normal non-oncogenic differentiation of the transformed tissues is possible. It is also preferred that the *Agrobacterium* harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, *Biotechnology*, 1:262, 1983; Hoekema, et al., *Nature*, 303:179, 1983). Such a binary system is preferred because it does not require integration into Ti plasmid in *Agrobacterium*.

Methods involving the use of *Agrobacterium* include, but are not limited to: 1) co-cultivation of *Agrobacterium* with cultured isolated protoplasts; 2) transformation of plant cells or tissues with *Agrobacterium*; or 3) transformation of seeds, apices or meristems with *Agrobacterium*.

In addition, gene transfer can be accomplished by in situ transformation by *Agrobacterium*, as described by Bechtold, et al., (*C. R. Acad. Sci. Paris*, 316:1194, 1993). This approach is based on the vacuum infiltration of a suspension of *Agrobacterium* cells.

The preferred method of introducing heterologous nucleic acid into plant cells is to infect such plant cells, an explant, a meristem or a seed, with transformed *Agrobacterium tumefaciens* as described above. Under appropriate conditions known to those skilled in the art, the transformed plant cells are grown to form shoots, roots, and develop further into plants.

A preferred vector(s) of the invention comprises a Ti plasmid binary system wherein the heterologous nucleic acid sequence encodes the BAS1 protein. Such a vector may optionally contain at least one other nucleic acid sequence that encodes a second factor or protein active in brassinolide synthesis or signaling, such as BIN1 or CHIBI2 and combinations thereof. Alternatively, two vectors can be utilized wherein each vector contains at least one heterologous nucleic acid sequence. Other brassinolide or ecdysteroid activity modifying genes can be utilized for construction of one or more vectors, in a similar manner.

Alternatively, heterologous nucleic acid can be introduced into a plant cell by contacting the plant cell using mechanical or chemical means. For example, the nucleic acid can be mechanically transferred by microinjection directly into plant cells by use of micropipettes. Alternatively, the nucleic acid may be transferred into the plant cell by using polyethylene glycol which forms a precipitation complex with genetic material that is taken up by the cell.

Heterologous nucleic acid can also be introduced into plant cells by electroporation (Fromm, et al, *Proc. Natl. Acad. Sci., U.S.A.*, 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing nucleic acid into a plant cell is high velocity ballistic penetration by small particles with the nucleic acid to be introduced contained either within the matrix of small beads or particles, or on the surface thereof (Klein, et al., *Nature* 327:70, 1987). Although, typically only a single introduction of a new nucleic acid sequence is required, this method particularly provides for multiple introductions.

Cauliflower mosaic virus (CaMV) may also be used as a vector for introducing heterologous nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants. Methods are also know for use of Tobacco mosaic virus as a vector to obtain expression of recombinant DNA (U.S. Pat. No. 5,955,647).

In another embodiment, the invention provides a method for genetically modifying a plant cell such that a plant, produced from the cell, is characterized as having modulated brassinolide synthesis or signaling. Modulated brassinolide activity includes a change in plant stature, leaf color and sensitivity to light compared with a wild type plant. The method includes introducing at least a BAS1-encoding polynucleotide of the invention into a plant cell to obtain a transformed plant cell and growing the transformed plant cell under conditions which permit expression of BAS1 polypeptide, thereby producing a plant having modulated brassinolide synthesis or signaling. The term "modulated" refers to increased or decreased brassinolide or ecdysteroid synthesis or signaling compared with a wild-type plant. For example, a plant having decreased brassinolide activity caused by overexpression of BAS1 is characterized by one or more of the following: hypersensitivity to far-red light in a PHYA background and lack of responsiveness in a phyA null background, etiolation with hypocotyls of near wild-type length in dark grown seedlings, and dwarfism with dark-green leaves in adult plants.

Decreased brassinolide or ecdysteroid activity can be achieved by induction or augmentation of bas1 gene expression or BAS1 polypeptide activity. Vectors encoding BAS1 polypeptide that are useful in the method of the invention are described herein. For example, bas1 gene expression under control of an inducible promoter or constitutive promoter can be used to increase production of BAS1 over levels found in wild-type plants.

Similarly, increased brassinolide or ecdysteroid activity can be achieved by inhibiting expression of endogenous bas1 gene or BAS1 polypeptide activity in the plant. BAS1 antisense or BAS1 dominant negative nucleic acid sequences can be used to inhibit bas1 gene expression or decrease wild-type BAS1 protein activity, respectively, for example.

For example, dominant-negative versions of BAS1 and/or other brassinolide synthesis or signaling regulatory genes could be expressed constitutively. Dominant-negative mutants are proteins that actively interfere with the function of a normal, endogenous protein. Thus, the action of a gene can be blocked without inactivating the structural gene itself or its RNA. This strategy has been successful for both signal transduction molecules and for transcription factors (e.g., Attardi, et al., *Proc. Natl. Acad. Sci. USA*, 90:10563, 1993; Lloyd, et al., *Nature*, 352:635, 1991; Logeat, et al., *EMBO J*, 10:1827, 1991: Mantovani, et al., *J Biol. Chem.*, 269: 20340, 1994; Ransone, et al., *Proc. Natl. Acad. Sci. USA*, 87:3806, 1990; Richardson, et al., *Mech. Dev.*, 45:173, 1994; Tsai, et al., *Genes Dev.*, 6:2258, 1992; Thomas et al., *Nature Genetics*, 17:58, 1997; Wittbrodt, J. And Rosa, F., *Genes and Development*, 8:1448, 1994; Kashles et al., *Mol. Cell. Biol*, 11:1454, 1991; Pierce & Kimelman, *Development*, 121:755, 1995).

In another embodiment, the invention includes a method of producing a genetically modified plant characterized as having dwarf adult stature with dark green foliage, including contacting a plant cell with a vector containing an exogenous nucleic acid sequence comprising at least one structural gene encoding a BAS1 polypeptide, operably associated with regulatory sequence that causes overexpression of the gene to obtain a transformed plant cell; producing a plant from the transformed plant cell; and selecting a plant exhibiting dwarf adult stature with dark green foliage, compared with wild type plants.

As used herein, the term "contacting" refers to any means of introducing the vector(s) into the plant cell, including chemical and physical means as described above. Preferably, contacting refers to introducing the nucleic acid or vector into plant cells (including an explant, a meristem or a seed), via *Agrobacterium tumefaciens* transformed with the heterologous nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part). Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxin and cytokinins. It is sometimes advantageous to add glutamic acid and proline to the medium, especially for such species as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see *Methods in Enzymology*, Vol. 118 and Klee, et al., *Annual Review of Plant Physiology*, 38:467, 1987). Utilizing the leaf disk-transformation-regeneration method of Horsch, et al, *Science*, 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by the taking of cuttings or by tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The inbred plant produces seed containing the newly introduced foreign gene(s). These seeds can be grown to produce plants that would produce the selected phenotype, e.g. dwarfism with darker-green foliage than wild type plants.

Parts obtained from the regenerated plant, such as flowers, seeds, leaves, branches, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Plants exhibiting modulated brassinolide synthesis or signaling can be selected by visual observation and by the methods disclosed in the Examples herein. The invention includes a plant produced by the method of the invention, including plant tissue, seeds, and other plant cells derived from the genetically modified plant.

In yet another embodiment, the invention provides a genetically modified plant comprising at least one exogenous nucleic acid sequence encoding a cytochrome P450, e.g., BAS1 polypeptide, in its genome or at least one regulatory sequence that modifies expression of endogenous cytochrome P450, e.g., bas1 gene and which is characterized as having modulated brassinolide activity, for example decreased brassinolide synthesis or signaling in the plant. The promoter sequence is operably linked with the structural gene. The promoter is an inducible promoter when induction of brassinolide activity is desired. For example, a plant cell and plant is produced as described herein and modulated brassinolide activity or signaling is induced in the plant by contacting the promoter, linked with a nucleic acid sequence encoding BAS1, with an appropriate inducer. Such inducible promoters are described above, and include those promoters preferably inducible by chemical means.

By "transformation" is meant a generic change induced in a cell following incorporation of new DNA (i.e. DNA exogenous to the cell). Where the cell is a mammalian cell, the genetic change is generally achieved by introduction of the DNA into the genome of the cell (i.e. stable). By "transformed cell" is meant a cell into which (or into an ancestor of which) has been introduced, by means of recombinant DNA techniques, a DNA molecule encoding cytochrome P450, e.g., BAS1. Transformation of a host cell with recombinant DNA may be carried out by conventional techniques as are well known to those skilled in the art.

In another embodiment, the invention provides a method for producing a genetically modified plant characterized as having increased disease or insect as compared to a plant which has not been genetically modified (e.g., a wild-type plant). The term "disease or insect" or "pathogen" or "insect" resistance refers to the ability to maintain a desirable phenotype upon exposure to infection, relative to a nontransgenic plant. The level of resistance can be determined by comparing the physical characteristics of the invention plant to nontransgenic plants that either have or have not been exposed to infection or insect infestation. Exemplary physical characteristics to observe include an increase in population of plants that have the ability to survive pathogen challenge, delayed lesion development, reduced lesion size, and the like. The term "disease" refers to a pathogen challenge caused any agent known to cause symptoms of infection in plants, including, but not limited to bacteria, nematodes, viruses, mycoplasmas, and fungi. In a preferred embodiment, the pathogen is a bacterial pathogen, including, but not limited to, *Pseudomonas*. Exemplary organisms include *Pseudomonas synringe* pv. *tomato* (Pst) and *Pseudomonas syringe* pv. *maculicola* (Psm). The term "increased resistance to pathogens" or "increased resistance to disease" refers to a level of resistance that an invention transgenic plant has to plant pathogens above a defined reference level such as the level of resistance displayed by nontransgenic plants of the same species. Thus, the increased resistance is measured relative to previously existing plants of the same species. In one embodiment, the resistance is substantially increased above the defined reference level greater than or equal to a 20% increase, preferably greater than or equal to a 50% increase, more preferably greater than or equal to a 75% increase, with the most preferred being a 95% increase and above. The phase "nontransgenic plant of the same species" means a plant of the same species that does not contain any heterologous transgenes, or does not contain any transgenes containing a sequence derived from BAS1. The term "heterologous nucleic acid sequence" as used herein refers to a nucleic acid foreign to the recipient plant host or, native to the host if the native nucleic acid is substantially modified from its original form. The levels of pathogen resistance can be determined using methods well known to one of skill in the art. These methods include bacterial resistance assays and fungal infection assays described in U.S. Pat. No. 5,530,187, herein incorporated by reference.

Preferably the transgenic plants are resistant to Coleoptera and Lepidoptera such as western corn root worm (*Diabrotica virgifera virgifera*), northern corn root worm (*Diabrotica longicornis barberi*), southern corn rootworm (*Diabrotica undecimpunctata howardi*), cotton bollworm, European corn borer, corn root webworm, pink bollworm and tobacco budworm. The transgenic plants are preferably monocotyledoneous or dicotyledoneous plants. Representative plant pests (e.g., insects) include but are not limited to Coleoptera: *Diabrotica, Melanotus, Agriotes, Limonius, Dalopius, Eleodes, Chaetocnema, Macrodactylus, Sphenophorus, Sitophilus, Lisorhoptrus, Oulema, Rhyzopertha, Prostephanus, Phyllophage, Cyclocephala, Popillia, Anthonomus, Zabrotes, Leptinotarsa;* Lepidoptera: *Heliothis, Ostrinia, Diatraea, Elasmopalpus, Papaipema, Agrotis, Loxagrotis, Euxoa, Peridroma saucia, Chorizagrotis, Spodoptera, Pseudaletia, Chilo, Busseola, Sesamia, Eldana, Maliarpha, Scirpophaga, Duataea, Rupela, Sitotroga cerealella, Sitroga, Plodia interpunctella, Crambus, Mythimna, Nola, Pectinophora, Acontia, Trichoplusia, Anticarsia, Pseudoplusia, Manduca, Leptinotarsa, Lema* Thysanoptera: *Frankliniella, Anaphothrips, Hercothrips, Stenothrips* Homoptera: *Dalbulus, Cicadulina, Rhopalosiphum, Melanaphis, Anuraphis, Prosapia, Nilaparvata, Sogatella, Laodelphax, Sogatodes, Nephotettix, Reciian, Cofana, Empoasca, Poophilus, Schizaphis, Sipha, Paratrioza, Empoasca, Ophilia. Scleroracus, Macrosteles, Circulifer, Aceratagallia, Agallia, Myzus, Macrosiphum, Aphis* Diptera: *Delia platura, Euxesta, Diopsis, Atherigona, Hydrellia, Orseolia, Chironomus, Contarinia* Orthoptera: *Melanoplus, Schistocerca, Sphenarium, Aneolamia* Isoptera: *Microtermes, Macrotermes, Allodontermes, Odontotermes* Heteroptera: *Nezara, Acrosternum, Euschistus, Blissus* Acarina: *Tetranychus, Paratetranychus, Oligonychus.*

Plant pathogens or insects, cause disease by weakening the plant by absorbing food from the plant cells, secreting toxins, enzymes, or growth regulating substances that disturb or kill the plant cells, or block the transport of food nutrients or water in the plant. The roots, stems, leaves, flowers, or fruits can be infected. The affected cells and tissues are weakened or destroyed, and cannot perform normal physiological functions, resulting in reduction of plant growth or death, and reducing crop quality or yield. The major causes of plant diseases are bacteria, mycoplasmas, viruses, nematodes, and fungi. Fugal species from a variety of genera affect plants, including *Fusarium, Pythium, Phytophthora, Verticillium, Rhizoctonia, Macrophonmina, Thielaviopsis, Sclerotinia,* and numerous others. Plant disease caused by fungi include pre- and post-emergence seedling damping-off, hypocotyl rots, root rots, crown rots, vascular wilt, and other symptoms. Nematodes harmful to plants include nematode species form the genera *Meloidogyne, Heterodera, Ditylenchus,* and *Pratylencus.* Plant diseases caused by nematodes include root galls, root rot, lesions, "stubby" root, stunting, and other rots and wilts. Some nematodes (e.g., Trichodorus, Lonoidorus, Xipenema) can serve as vectors for virus diseases in a number of plants including Prunus, grape, tobacco, and tomato.

The method of the invention comprises the steps of introducing at least one-nucleic acid sequence encoding BAS1 into a plant cell to obtain a transformed plant cell, wherein the nucleic acid sequence is operably associated with a promoter; producing a plant from the transformed plant cell under conditions which allow expression of BAS1 polynucleotide to produce BAS1 polypeptide; and thereafter selecting a plant exhibiting increased pathogen resistance. The plant may be either a magnitude or a dicot. Examples of monocotyledonous plants include, but are not limited to, asparagus, field and sweet corn, barley, wheat, rice (e.g., *Japonica* or *Indica*), sorghum, onion, pearl millet, rye and oats. Examples of dicotyledonous plants include, but are not limited to tomato, tobacco, cotton, rapist, field beans, soybeans, potatoes, grapes, strawberries, peppers, lettuce, peas, alfalfa, clover, Cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, sequoia, cedar, oak, and the like.

The term "genetic modification" as used herein refers to the introduction of one or more heterologous nucleic acid sequences into one or more plant cells, to provide sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell.

As used herein, the term "plant" refers to either a whole plant, a plant part, a plant cell, or a group of plant cells, such as plant tissue, for example. Plantlets are also included within the meaning of "plant" Plants included in the invention are any plants amenable to transformation techniques, including angiosperms, gymnosperms, monocotyledons and dicotyledons.

The term "heterologous nucleic acid sequence" has been defined above. Any nucleic acid sequence of interest may be used with the subject invention. For example, the term includes a nucleic acid originating in the host species, where such sequence is operably linked to a promoter that differs from the natural or wild-type promoter. In the broad method of the invention, at least one nucleic acid sequence encoding BAS1 polypeptide is associated with a suitable promoter. It may be desirable to introduce more than one copy of BAS1 polynucleotide into a plant for enhanced BAS1 expression. For example, multiple copies of the gene would have the effect of increasing production of BAS1 polypeptide in the plant allowing for greater disease or insect.

Genetically modified plants of the present invention are produced by introducing into a plant cell, a vector including at least one nucleic acid sequence encoding BAS1. To be effective once introduced into plant cells, the BAS1 nucleic acid sequence must be operably associated with a promoter which is effective in the plant cells to cause transcription of BAS1. Additionally, a polyadenylation sequence or transcription control sequence, also recognized in plant cells may also be employed. It is preferred that the vector harboring the nucleic acid sequence to be inserted also contain one or more selectable marker genes so that the transformed cells can be selected from nontransformed cells in culture, as described herein.

The expression of BAS1 polynucleotides in the present invention may be driven by a number of promoters. The endogenous, or native promoter of an BAS1 may be utilized for transcriptional regulation of the gene, or a heterologous promoter that is a foreign regulatory sequence may be utilized. For plant expression vectors, suitable viral promoters include the 35S RNA and 19S RNA promoters of CaMV (Brisson et al, *Nature* 310:511, 1984; Odell et al., *Nature* 313:810, 1985); the full-length transcript promoter from Figwort Mosaic Virus (FMV) (Gowda et al., *J Cell Biochem.* 13D:301, 1989) and the coat protein promoter to TMV (Takamatsu et al., *EMBO J* 6:307, 1987). Alternatively, plant promoters such as the light-inducible promoter from the small subunit of ribulose bis-phosphate carboxylase (ss-RUBISCO) (Coruzzi et al., *EMBO J* 3:1671, 1984; Broglie et al., *Science* 224:838, 1984); mannopine synthase promoter (Velten et al., *EMBO J* 3:2723, 1984) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley et al., *Mol. Cell. Biol.* 6:559, 1986; Severin et al., *Plant Mol. Biol,* 15:827, 1990) may be used.

Promoters useful in the invention include both natural constitutive and inducible promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett et al., *Proc. Natl. Acad Sci. U.S.A.* 90:4567, 1993); In2-1 and In2-2 regulator sequences which are activated by substituted benzenesulfonamides, e.g., herbicide safeners (Hershey et al., *Plant Mol. Biol,* 17:679, 1991); and the GRE regulatory sequences which are induced by glucocorticoids (Schena et al., *Proc. Natl. Acad. Sci. U.S.A.* 88:10421, 1991)(See Example 10). Other promoters, both constitutive and inducible will be known to those of skill in the art.

The particular promoter selected should be capable of causing sufficient expression to result in the production of an effective amount of structural gene product, e.g., BAS1 polypeptide, to cause increased disease or insect, ultimately resulting in increased plant yield. The promoters used in the vector constructs of the present invention may be modified, if desired, to affect their control characteristics.

Tissue specific promoters may also be utilized in the present invention. An example of a tissue specific promoter is the promoter active in shoot meristems (Atanassova et al., *Plant J* 2:291, 1992). Other tissue specific promoters useful in transgenic plants, such as the cdc2a promoter and cyc07 promoter, will be known to those of skill in the art. (See, for example, Ito et al., *Plant Mol. Biol,* 24:863, 1994; Martinez et al., *Proc. Natl. Acad. Sci. USA* 89:7360, 1992; Medford et al., *Plant Cell* 3:359, 1991; Terada et al., *Plant Journal,* 3:241, 1993; Wissenbach et al., *Plant Journal* 4:411, 1993). There are promoters known which limit expression to particular plant parts or in response to particular stimuli (e.g., the patatin promoters or the promoters for the large or small subunits of ADP glucose pyrophosphorylase). These promoters which limit expression, such as those that direct expression to roots, could be operably associated with BAS1 to direct expression primarily in the tuber. One skilled in the art will know of many such plant part-specific promoters which would be useful in the present invention.

Promoters used in the nucleic acid constructs of the present invention may be modified, if desired, to affect their control characteristics. For example, the CaMV 35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CAMV 35S" promoter thus includes variations of CaMV 35S promoter, e.g., promoters derived by means of ligation with operator regions, random or controlled mutagenesis, etc. Furthermore, the promoters may be altered to contain multiple "enhancer sequences" to assist in elevating gene expression.

Alternatively, the promoters utilized may be selected to confer specific expression of BAS1 in response to disease such as fungal infection. The infection of plants by fungal pathogens activate defense-related or pathogenesis-related (PR) genes which encode (1) enzymes involved in phenylpropanoid metabolism such as phenylalanine ammonia lyase, chalcone synthase, 4-coumarate coA ligase and coumaric acid 4-hydroxylase, (2) proteins that modify plant cell walls such as hydroxyproline-rich glycoproteins, glycine-rich proteins, and peroxidases, (3) enzymes, such as chitinases and glucanases, that degrade the fungal cell wall, (4) thaumatin-like proteins, or (5) proteins of as yet unknown function. The defense-related or PR genes have been isolated and characterized from a number of plant species. The promoters of these genes may be used to obtain expression of BAS1 in transgenic plants when such plants are challenged with a pathogen, particularly a fungal pathogen such as Pi. The particular promoter selected should be capable of causing sufficient expression of BAS1 to result in the production of an effective amount of polypeptide.

Optionally, a selectable marker may be associated with the nucleic acid sequence to be inserted. The term "marker" has been defined above. Preferably, the marker gene is an antibiotic resistance gene whereby the appropriate antibiotic can be used to select for transformed plant cells from among plant cells that are not transformed. Examples of suitable selectable markers are described above. Preferably, the marker gene is an antibiotic resistance gene whereby the appropriate antibiotic can be used to select for transformed cells from among cells that are not transformed. Examples of suitable selectable markers for use in plants include adenosine deaminase, dihydrofolate reductase, hygromycin-B-phosphotransferase, thymidine kinase, xanthine-guanine phospho-ribosyltransferase and amino-glycoside 3'-O-phosphotransferase II (kanamycin, neomycin and G418 resistance). Other suitable markers will be known to those of skill in the art Vector(s) employed in the present invention for transformation of plant cells comprise a nucleic acid sequence encoding BAS1 polypeptide, operably associated with a promoter. To effect a transformation process in accordance with the present invention, it is first necessary to construct a suitable vector and properly introduce it into the plant cell. Details of the construction of vectors utilized herein are known to those skilled in the art of plant genetic engineering.

BAS1 nucleic acid sequences utilized in the present invention can be introduced into plant cells using Ti plasmids of *Agrobacterium tumefaciens,* root-inducing (Ri) plasmids, and plant virus vectors. (For reviews of such techniques see, for example, Weissbach & Weissbach, *Methods for Plant Molecular Biology,* Section VIII, pp. 421–463, Academic Press, NY, 1988; Grierson & Corey, *Plant Molecular Biology,* 2d Ed., Ch. 7–9, Blackie, London, 1988; and Horsch et al., *Science,* 227:1229, 1985; each incorporated herein by reference). In addition to plant transformation vectors derived from the Ti or root-inducing (Ri) plasmids of *Agrobacterium,* alternative methods of transformation may be utilized including the use of liposomes, electroporation, chemicals that increase free nucleic acid uptake, transformation using viruses or pollen and the use of biolistic transformation.

One of skill in the art will be able to select an appropriate vector for introducing the BAS1 polynucleotide sequence in a relatively intact state. Thus, any vector which will produce a plant carrying the introduced nucleic acid sequence should be sufficient. Even use of a naked piece of nucleic acid would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, *Methods of Enzymology,* Vol. 153, Wu and Grossman, Eds., Academic Press, 1987, incorporated herein by reference). As used herein, the term "transformation" means alteration of the genotype of a host plant by the introduction of BAS1 nucleic acid sequence.

For example, an BAS1 nucleic acid sequence can be introduced into a plant cell utilizing *Agrobacterium tumefaciens* containing the Ti plasmid, as mentioned briefly above. In using an *A. tumefaciens* culture as a transformation vehicle, it is advantageous to use a nononcogenic strain of *Agrobacterium* as the vector carrier so that normal nononcogenic differentiation of the transformed tissues is possible. It is also preferred that the *Agrobacterium* harbor a binary Ti plasmid system. Such a binary system comprises 1) a first Ti plasmid having a virulence region essential for the introduction of transfer nucleic acid (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, *Biotechnology* 1:262, 1983; Hoekema et al., *Nature* 303:179, 1983). Such a binary system is preferred because it does not require integration into the Ti plasmid of *Agrobacterium,* which is an older methodology.

Methods involving the use of *Agrobacterium* in transformation according to the present invention include, but are not limited to: 1) cocultivation of *Agrobacterium* with cultured isolated protoplasts; 2) transformation of plant cells or tissues with *Agrobacterium;* or 3) transformation of seeds, apices or meristems with *Agrobacterium.*

In addition, gene transfer can be accomplished by in plant a transformation by *Agrobacterium,* as described by Bechtold et al., (*C. R. Acad. Sci. Paris* 316:1194, 1993) and exemplified in the Examples herein. This approach is based on the vacuum infiltration or dipping of a suspension of *Agrobacterium* cells.

The preferred method of introducing BAS1 polynucleotide into plant cells is to infect such plant cells, an explant, a meristem or a seed, with transformed *Agrobacterium tumefaciens* as described above and in the Examples. Under appropriate conditions known in the art, the transformed plant cells are grown to form shoots, roots, and develop further into plants.

Alternatively, BAS1 polynucleotide can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

BAS1 polynucleotide can also be introduced into plant cells by electroporation (Fromm et al., *Proc. Natl. Acad. Sci. U.S.A.* 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing BAS1 polynucleotide into a plant cell is high velocity ballistic penetration by small particles with the nucleic acid to be introduced contained either within the matrix of such particles, or on the surface thereof (Klein et al., *Nature* 327:70, 1987). Bombardment transformation methods are also described in Sanford et al. (*Techniques* 3:3–16, 1991) and Klein et al. (*Bio/Techniques* 10:286, 1992). Although, typically, only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral nucleic acid genome is inserted into a parent bacterial plasmid creating a recombinant nucleic acid molecule which can be propagated in bacteria. After cloning, the recombinant plasmid again may be cloned and further modified by introduction of the desired nucleic acid sequence (e.g., the BAS1 sequence). The modified viral portion of the recombinant plasmid is then excised from the parent bacterial plasmid, and used to inoculate the plant cells or plants.

As used herein, the term "contacting" refers to any means of introducing BAS1 into the plant cell, including chemical and physical means as described above. Preferably, contacting refers to introducing the nucleic acid or vector into plant cells (including an explant, a meristem or a seed), via *Agrobacterium tumefaciens* transformed with the BAS1 encoding nucleic acid as described above.

Normally, a transformed plant cell is regenerated to obtain a whole plant from the transformation process. The immediate product of the transformation is referred to as a "transgenote. The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species, but generally the process is initiated by first providing a suspension of protoplasts. In certain species, plant formation can be induced from the protoplast suspension, followed by ripening and germination as natural plant. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, the genotype, and the history of the culture. If these variables are controlled, regeneration is reproducible.

Regeneration also occurs from plant callus, explants, organs or parts. Transformation can be performed in the context of organ or plant part regeneration. (see *Methods in Enzymology,* Vol. 118, 1987, and Klee et al., *Annual Review* of *Plant Physiology*, 38:467, 1987). Utilizing the leaf disk-transformation-regeneration method of Horsch et al., *Science* 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, the mature transgenic plants is self crossed to produce a homozygous inbred plant. The resulting inbred plant produces seed containing the newly introduced foreign gene(s). These seeds can be grown to produce plants that would produce the selected phenotype, e.g., increased yield.

Parts obtained from regenerated plant, such as flowers, seeds, leaves, branches, roots, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

After selecting the transformed cells, one can confirm expression of the desired heterologous gene. Simple detection of mRNA encoded by the inserted DNA can be achieved by well known methods in the art, such as Northern blot hybridization. The inserted sequence can be identified by Southern blot hybridization, as well.

Plants exhibiting increased disease or insect as compared with wild-type plants can be selected by visual observation. (See also U.S. Pat. No. 5,530,187, incorporated herein by reference.) The invention includes plants produced by the method of the invention, as well as plant tissue and seeds.

In yet another embodiment, the invention provides a method for genetically modifying a plant cell such that a plant, produced from the cell, is characterized as having increased disease or insect as compared with a wild-type plant. The method includes introducing at least one nucleic acid sequence encoding BAS1 polypeptide into a plant cell a transformed plant cell; growing the transformed plant cell under conditions which allow expression of BAS1 polypeptide thereby producing a plant having increased disease resistance. Conditions such as environmental and promoter inducing conditions vary from species to species, but should be the same within a species.

In another embodiment, the invention provides a method of producing a plant characterized as having increased disease or insect by introducing BAS1 polynucleotide into a plant cell to obtain a transformed cell, and then growing the transformed plant cell under conditions which permit expression of BAS1 polypeptide to produce a plant with increased disease or insect. The term "expression" refers to an increase in transcription of BAS1 DNA or translation of BAS1 mRNA or activity of BAS1 polypeptide.

In yet another embodiment, the invention provides a method of producing a plant characterized by having increased disease or insect as compared to a wild type plant by contacting a susceptible plant with an BAS1 promoter-inducing amount of an agent which induces BAS1 gene expression, wherein induction of BAS1 gene expression results in production of a plant having increased disease or insect as compared to a plant not contacted with the agent. The agent can induce endogenous BAS1 gene expression, for example. In a preferred embodiment, the plant is a transgenic plant containing a nucleic acid encoding an inducible promoter operably linked to nucleic acid encoding BAS1. Examples of inducible promoters useful in plants include those induced by chemical means, such as the yeast metallothionein promoter which is activated by copper ions (Mett, et al., *Proc. Natl. Acad. Sci. U.S.A.* 90:4567, 1993); In2-1 and In2-2 regulator sequences which are activated by substituted benzenesulfonamides, e.g., herbicide safeners (Hershey, et al., *Plant Mol. Biol.* 17:679, 1991); and the GRE regulatory sequences which are induced by glucocorticoids (Schena et al., *Proc. Natl. Acad. Sci. U.S.A.* 88:10421, 1991). The term promoter inducing amount refers to that amount of agent necessary to elevate BAS1 gene expression above BAS1 expression in a plant cell not contacted with the agent. For example, a transcription factor or a chemical agent may be used to elevate gene expression from BAS1 native promoter. The invention method envisions contacting cells containing endogenous BAS1 promoter or recombinantly produced BAS1 promoter.

Screen for Identifying Novel Disease or Insect Resistance Genes

The invention provides a method of identifying novel disease or insect resistance genes related to BAS1 by probing a nucleic acid library with at least a fragment of an isolated polynucleotide encoding BAS1, and selecting those clones that hybridize with the fragment. Novel disease or insect resistant genes, such as homologs of BAS1 are identified by any of a number of methods. The nucleotide sequence encoding a novel disease or insect gene can be isolated according to any one of a variety of methods well known to those of ordinary skill in the art. For example, DNA encoding a BAS1 homolog can be isolated from either a cDNA library or from a genomic DNA library (see, e.g., Sambrook et al., 1989. *Molecular Cloning: A Laboratory Manual*, 2nd Ed., Cold Spring Harbor Laboratory Press, Cold Spring Harbor, N.Y.). In one embodiment, a fragment of a polynucleotide encoding BAS1 may be used as a hybridization probe with a cDNA library from the target organism of interest, where low stringency conditions are used. The probe may be a large fragment, or one or more short degenerate primers. In a preferred embodiment, the probe is at least eight nucleotides in length.

Nucleic acids having sequence similarity are detected by hybridization under low stringency conditions, for example, at 50/C and 10×SSC (0.9 M saline/0.09 M sodium citrate) and remain bound when subjected to washing at 55/C in 1×SSC. Sequence identity can be determined by hybridization under more stringent conditions, for example, at 50/C or higher and 0.1×SSC (9 mM saline/0.9 mM sodium citrate). By using probes, particularly labeled probes of DNA sequences, one can isolate homologous or related genes. The source of homologous genes may be any species, e.g. plant species, primate species, particularly human; rodents, such as rats and mice, canines, felines, bovines, ovines, equines, yeast, and nematodes.

Alternatively, the DNA encoding a novel disease or insect gene can be isolated using standard polymerase chain reaction (PCR) amplification of synthetic oligonucleotide primers, e.g., as described in Mullis et al., U.S. Pat. No. 4,800,159, or expression cloning methods well known in the art (see, e.g., Sambrook et al., 1989, *Molecular Cloning: A Laboratory Manual*, 2nd Ed., Cold Spring Harbor Laboratory Press, Cold Spring Harbor, N.Y.). One of skill in the art can readily design primers for PCR amplification based on the sequence of a polynucleotide encoding BAS1 polypeptide.

Between plant species, e.g. monocotyledons, dicotyledons, and woody species, homologs typically have substantial sequence similarity, i.e. at least 75% sequence identity between nucleotide sequences. Sequence similarity is calculated based on a reference sequence, which may be a subset of a larger sequence, such as a conserved motif, coding region, or flanking region, for example. A reference sequence will usually be at least about 18 nucleotides (nt) long, more usually at least about 30 nt long, and may extend to the complete sequence that is being compared. Algorithms for sequence analysis are known in the art, such as BLAST, described in Altschul et al. (1990) *J Mol. Biol.* 215:403–10. The sequences provided herein are essential for recognizing BAS1 related and homologous proteins in database searches.

Antibodies

The BAS1 polypeptides of the invention can be used to produce antibodies which are immunoreactive or bind to epitopes of the BAS1 polypeptides. Antibodies that consist essentially of pooled monoclonal antibodies with different epitopic specificities, as well as distinct monoclonal antibody preparations, are provided.

The preparation of polyclonal antibodies is well-known to those skilled in the art. See, for example, Green et al., Production of Polyclonal Antisera, in: *Immunochemical Protocols* (Manson, ed.), pages 1–5 (Humana Press 1992); Coligan et al., Production of Polyclonal Antisera in Rabbits, Rats, Mice and Hamsters, in: *Current Protocols in Immunology*, section 2.4.1 (1992), which are hereby incorporated by reference.

The preparation of monoclonal antibodies likewise is conventional. See, for example, Kohler & Milstein, 1975, Nature 256:495; Coligan et al., sections 2.5.1–2.6.7; and Harlow et al., in: *Antibodies: a Laboratory Manual*, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., Purification of Immunoglobulin G (IgG), in: *Methods in Molecular Biology*, Vol.10, pages 79–104 (Humana Press 1992).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisonhoff et al., 1960, *Arch. Biochem. Biophys.* 89:230, Porter, 1959, *Biochem. J* 73:119; Edelman et al., 1967, *Methods in Enzmology*, Vol. 1, page 422 (Academic Press); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., 1972, *Proc. Nat'l Acad. Sci. USA* 69:2659. Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al, 1991, *Methods: a Companion to Methods in Enzymology*, Vol. 2, page 97; Bird et al., 1988, *Science* 242:423–426; Ladner et al., U.S. Pat. No.4,946,778; Pack et al., 1993, *Bio/Technology* 11:1271–77; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology*, Vol. 2, page 106 (1991).

Antibodies that bind to a BAS1 polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Genetically Modified Plants

In one embodiment, the invention provides a genetically modified plant comprising at least one heterologous nucleic acid sequence encoding BAS1 in its genome, wherein the BAS1-encoding sequence modulates brassinolide synthesis or signaling in the plant. The plant may also be characterized as having modulated phytoecdysteroid activity. The plant is therefore characterized as having modulated brassinolide or phytoecdysteroid activity. Also included herein are plant cells and plant tissue, all derived from the genetically modified plant of the invention. In addition, seeds which can germinate into a genetically modified plant as described herein are also provided.

The term "genetic modification" as used herein refers to the introduction of one or more heterologous nucleic acid sequences into one or more plant cells, which can generate whole, sexually competent, viable plants. The term "genetically modified" as used herein refers to a plant which has been generated through one of the aforementioned processes. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including monocotyledonous and dicotyledonous plants, as well as conifers, and the like.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Woody species include poplar, aspen, pine, sequoia, cedar, cottonwood, sweetgum, acacia, oak, and the like. BAS1 gain-of-function mutants in such woody species produce trees that are more compact and darker green than plants not overexpressing bas1 gene. Furthermore, a range of phenotypes is seen in such transgenic plants (e.g., depending on the degree of overexpression) from extreme dwarfs to those which are slightly more compact and dark green, allowing the selection of "ideal" dwarfs that can be bred indefinitely. In addition to trees and other ornamentals, bas1 mutant turf grass can be produced to obtain more compact, dark-green lawns (e.g., that need little mowing). The invention dwarf plants, unlike conventional dwarf plants, are produced without application of expensive exogenous organic compounds throughout the life of the plant, which chemicals may be illegal to apply under certain conditions.

The term "heterologous nucleic acid sequence" as used herein refers to at least one structural gene operably associated with a regulatory sequence such as a promoter. The nucleic acid sequence originates in a foreign species, or, in the same species if substantially modified from its original form. For example, the term "heterologous nucleic acid sequence" includes a nucleic acid originating in the same species, where such sequence is operably linked to a promoter that differs from the natural or wild-type promoter.

As used herein, the term "nucleic acid sequence" refers to a polymer of deoxyribonucleotides or ribonucleotides, in the form of a separate fragment or as a component of a larger construct. DNA encoding the proteins utilized in the method of the invention can be assembled from cDNA fragments or from oligonucleotides which provide a synthetic gene which is capable of being expressed in a recombinant transcriptional unit. Polynucleotide or nucleic acid sequences of the invention include DNA, RNA and cDNA sequences (see description previously).

Antisense Polynucleotides

Plants having increased ecdysteroid or brassinolide levels and/or activity can be achieved by introduction of antisense molecules into a plant cell from which a transformed or genetically modified plant is produced. This approach also includes, for example, antisense nucleic acid, ribozymes, or triplex agents to block transcription or translation of BAS1 mRNA, either by masking that mRNA with an antisense nucleic acid or triplex agent, or by cleaving it with a ribozyme.

In one embodiment, the invention includes a genetically modified plant having a transgene disrupting or interfering with expression of bas1 gene, chromosomally integrated into the genome of the plant. A "transgene" is any piece of DNA which is inserted by artifice into a cell, and becomes part of the genome of the organism or plant which develops from that cell. Such a transgene may include a gene which is partly or entirely heterologous (i.e., foreign) to the transgenic organism, or may represent a gene homologous to an endogenous gene of the organism. As used herein, the term "transgene" means a DNA sequence that includes one or more selected DNAs to be expressed in a genetically modified or transgenic plant that is partly or entirely heterologous, i.e., foreign, to the transgenic plant, or homologous to an endogenous gene of the transgenic plant, but is designed to be inserted into the plant's genome at a location that differs from that of the natural gene. A transgene includes one or more promoters and any other DNA, such as introns, necessary for expression of the selected DNA, all operably linked to the selected DNA, and may include an enhancer sequence.

The invention includes a method of producing a genetically modified plant characterized as being hyper-responsive to brassinolide by contacting a plant cell with a vector containing a nucleic acid sequence including at least a structural gene disrupting or interfering with expression of BAS1 polypeptide, wherein the gene is operably associated with a promoter, to obtain a transformed plant cell; producing a plant from the transformed plant cells; and selecting a plant exhibiting hyper-responsiveness to brassinolide in a light dependent manner. Hyper-responsiveness to brassinolide can be identified as demonstrated in the Examples herein, e.g., visual observation of transgenic plant hypocotyl development versus wild-type plant hypocotyl development in seedlings.

The method of producing a genetically modified plant characterized as having hyper-responsiveness to brassinolide includes contacting a plant cell with a vector containing a BAS1 antisense nucleic acid sequence or a nucleic acid sequence encoding a dominant negative form of BAS1, operably associated with a promoter, and raising plants obtained from such plant cells in light.

Antisense nucleic acids are DNA or RNA molecules that are complementary to at least a portion of a specific mRNA molecule (Weintraub, 1990, *Scientific American* 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target BAS1-producing cell. The use of antisense methods to inhibit the in vitro translation of genes is well known in the art (Marcus-Sakura, 1988, *Anal. Biochem.* 172:289). Virus can also be used for antisense suppression (Angell and Balcombe, *Embo J.,* 16:3675, 1997).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., 1991, *Antisense Res. and Dev.* 1(3):227; Helene, C., 1991, *Anticancer Drug Design* 6(6):569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988, *J. Amer. Med. Assn.* 260:3030). A major advantage of this approach is that, because they are sequence-specific, only mRNAs with particular sequences are inactivated.

There are two basic types of ribozymes namely, tetrahymena-type (Hasselhoff, 1988, *Nature* 334:585) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to *tetrahymena*-type ribozymes for inactivating a specific mRNA species and 18-based recognition sequences are preferable to shorter recognition sequences.

Dominant Negative Mutations

In another embodiment of the present invention, a nucleotide sequence encoding a BAS1 dominant negative protein is provided. For example, a genetic construct that contain such a dominant negative encoding gene may be operably linked to a promoter, such as a tissue-specific promoter. Examples of such promoters and methods of use are described above.

Such constructs are useful in methods for modulating brassinolide activity or controlling stature in a plant. For example, a method of the invention includes transforming a plant cell or tissue with a genetic construct encoding a dominant negative BAS1 protein and suitable promoter in operable linkage and expressing the dominant negative encoding bas1 gene, thereby modulating brassinolide activity in the plant by interfering with wild-type BAS1 activity.

Screen for BAS1 Agonists or Antagonists

In another embodiment, the invention provides a method for identifying a compound that modulates BAS1 protein activity or gene expression. The method includes incubating components comprising the compound, BAS1 polypeptide or a recombinant cell expressing BAS1 polypeptide, under conditions sufficient to allow the components to interact and determining the effect of the compound on BAS1 activity or expression. The effect of the compound on BAS1 activity can be measured by a number of assays, and may include measurements before and after incubating in the presence of the compound. Compounds that affect BAS1 activity or gene expression include peptides, peptidomimetics, polypeptides, chemical compounds and biologic agents. Assays include Northern blot analysis of BAS1 mRNA (e.g., for gene expression) and Western blot analysis (e.g., for protein activity).

Incubating includes conditions which allow contact between the test compound and BAS1 polypeptide or with a recombinant cell expressing BAS1 polypeptide. Contacting includes in solution and in solid phase, or in a cell. The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008–1012, 1985), allele-specific oligonucleotide (ASO) probe analysis (Conner, et al., Proc. Natl. Acad. Sci. USA 4, 80:278, 1983), oligonucleotide ligation assays (OLAs) (Landegren, et al., Science 241:1077, 1988), and the like. Molecular techniques for DNA analysis have been reviewed (Landegren, et al., Science 242:229–237, 1988).

The invention provides a method for identifying a compound which can modulate a BAS1 activity. The method includes incubating BAS1 polypeptide or a recombinant cell expressing a BAS1 polypeptide or variant thereof, and a test compound, under conditions sufficient to allow the components to interact, and measuring the effect of the compound on the activity or expression of BAS1. Compounds that affect BASI activity or gene expression include peptides, polypeptides, pepidomimetics, chemical compounds and biological agents.

"Incubating" includes conditions which allow contact between the test compound and BAS1 polypeptide. "Contacting" includes in solution and solid phase. The test compound may also be a combinatorial library for screening a plurality of compounds. A variety of other agents may be included in the screening assay. These include agents like salts, neutral proteins, e.g., albumin, detergents, etc that are used to facilitate optimal protein-protein binding and/or reduce nonspecific or background interactions. Reagents that improve the efficiency of the assay, such as protease inhibitors, nuclease inhibitors, anti-microbial agents, etc., may be used. The mixture of components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 10 hours will be sufficient.

Compounds that are nucleic acid in nature identified in the method of the invention can be further evaluated, detected, cloned, sequenced, and the like, either in solution or after binding to a solid support, by any method usually applied to the detection of a specific DNA, such as PCR, oligomer restriction (Saiki et al., 1985, Bio/Technology, 3:1008–1012), allele-specific oligonucleotide (ASO) probe analysis (Conner et al., 1983, Proc. Natl. Acad. Sci. USA 80:278), oligonucleotide ligation assays (OLAs) (Landegren et al., 1988, Science 241:1077), and the like. Molecular techniques for DNA analysis have been reviewed (Landegren et al., 1988, Science 242:229–237).

Candidate compounds that affect BAS1 activity include chemical compounds. One class is organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups.

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents are also found among biomolecules including, but not limited to: peptides, saccharides, fatty acids, steroids, purines, pyrimidines, derivatives, structural analogs or combinations thereof.

A compound can affect reporter gene expression by either stimulating or inhibiting the expression of the reporter gene. A compound "inhibits" reporter gene expression if the level of transcripts or protein product produced from the reporter gene is decreased as compared with the level in the absence of the test compound. A compound "stimulates" reporter gene expression if the if the level of transcripts or protein product produced from the reporter gene is increased.

One of skill in the art can identify a number of reporter genes for use in the screening method of the invention. Examples of reporter genes of use with the invention are lacZ, luciferase, chloramphenicol acetyltransferase, beta-glucuronidase and green fluorescent protein.

The effect of the compound on the reporter gene transcription can be measured by assessing the expression of the reporter by methods well known in the art (e.g., Northern blots; EMSA). Alternatively or the production of protein product from the reporter gene can be measured by methods well known in the art (e.g., ELISA or RIA; Western blots; SDS-PAGE).

The invention further provides a method for identifying a cellular protein that binds to BAS1 polypeptide or a variant thereof, by incubating at least one cellular protein and invention BAS1 polypeptide or a variant thereof under conditions sufficient for the components to interact, separating a complex of the BAS1 polypeptide and a putative binding protein from the unbound BAS1, and isolating the protein (e.g., a 2-hybrid system).

In a preferred embodiment, an isolated cellular protein is utilized. However, partially purified proteins, fractions of cell extracts, whole cell extracts, or intact cells may be utilized with the method of the invention. "Incubating" includes conditions which allow contact between the cellular component and the BAS1 polypeptide. The term "interact"

includes in solution and solid phase, and includes any complex formation or binding of the cellular component to the BAS1 polypeptide. Interact also includes any enzymatic interaction wherein the cellular component performs a biochemical modification of the BAS1 polypeptide.

The complex of the cellular component with a BAS1 polypeptide can be separated from uncomplexed BAS1 polypeptide by conventional means, well known to one of skill in the art. The presence of cellular component bound to BAS1 can be accomplished by size separation, physical separation, or other standard methods. For example, nondenaturing gel electrophoresis can be used to separate BAS1 complexed with a cellular component from uncomplexed BAS1.

Once the complex has been isolated, the cellular component can be isolated and characterized by means well known in the art. For example, if the cellular component is a protein, the protein can be sequenced using methodology well known in the art. Polynucleotide encoding the protein can be produced using DNA synthesis technology. The polynucleotide can then be inserted into a vector using or molecular techniques well known in the art, and transformed into host cells using the techniques described above. Following transformation, large amounts of the protein may be isolated and purified in accordance with conventional ways. For example, lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell".

Alternatively, BAS1-encoding nucleic acid sequences can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

BAS1-encoding nucleic acid sequences can also be introduced into plant cells by electroporation (Fromm, et al., *Proc. Natl. Acad. Sci., U.S.A.*, 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing BAS1-encoding nucleic acid into a plant cell is high velocity ballistic penetration by small particles with the nucleic acid to be introduced contained either within the matrix of such particles, or on the surface thereof (Klein, et al., *Nature* 327:70, 1987). Bombardment transformation methods are also described in Sanford, et al. (*Techniques* 3:3–16, 1991) and Klein, et al. (*Bio/Techniques* 10:286, 1992). Although, typically only a single introduction of a new nucleic acid sequence is required, this method particularly provides for multiple introductions.

As used herein, the term "contacting" refers to any means of introducing bas1 into the plant cell, including chemical and physical means as described above. Preferably, contacting refers to introducing the nucleic acid or vector into plant cells (including an explant, a meristem or a seed), via *Agrobacterium tumefaciens* transformed with the BAS1-encoding nucleic acid as described above.

Screen for Identifying Novel Brassinolide-signaling and/or Response Genes

The invention provides a method of identifying novel brassinolide-signaling and/or response genes related to BAS1 by probing a nucleic acid library with at least a fragment of an isolated polynucleotide encoding BAS1, and selecting those clones that hybridize with the fragment. Novel brassinolide inhibiting genes, such as homologs of bas1, are identified by any of a number of methods. The nucleotide sequence encoding a novel brassinolide response gene can be isolated according to any one of a variety of methods well known to those of ordinary skill in the art. For example, DNA encoding a BAS1 homolog can be isolated from either a cDNA library or from a genomic DNA library (see, e.g., Sambrook et al., 1989. *Molecular Cloning: A Laboratory Manual,* 2nd Ed., Cold Spring Harbor Laboratory Press, Cold Spring Harbor, N.Y.). In one embodiment, a fragment of a polynucleotide encoding BAS1 may be used as a hybridization probe with a cDNA library from the target organism of interest, where low stringency conditions are used. The probe may be a large fragment, or one or more short degenerate primers. In a preferred embodiment, the probe is at least eight nucleotides in length.

Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under more stringent conditions, for example, at 50° C. or higher and 0.1×SSC (9 mM saline/0.9 mM sodium citrate). By using probes, particularly labeled probes of DNA sequences, one can isolate homologous or related genes. The source of homologous genes may be any species, e.g. plant species, primate species, particularly human; rodents, such as rats and mice, canines, felines, bovines, ovines, equines, yeast, and nematodes.

Alternatively, the DNA encoding a novel brassinolide synthesis or signaling gene can be isolated using standard polymerase chain reaction (PCR) amplification of synthetic oligonucleotide primers, e.g., as described in Mullis et al., U.S. Pat. No. 4,800,159, or expression cloning methods well known in the art (see, e.g., Sambrook et al., 1989, *Molecular Cloning: A Laboratory Manual,* 2nd Ed., Cold Spring Harbor Laboratory Press, Cold Spring Harbor, N.Y.). One of skill in the art can readily design primers for PCR amplification based on the sequence of a polynucleotide encoding BAS1 polypeptide.

Yet another alternative method for identifying homologous or related genes utilizes the so-called "two-hybrid" system of Fields & Song described in U.S. Pat. No. 5,283,173. The two-hybrid system involves the use of two chimeric genes which encode hybrid proteins to test for an interaction between a known protein and protein of interest. The first chimeric gene codes for a BAS1 polypeptide, or functional fragment thereof, fused to the DNA-binding domain of a transcriptional activator. The second chimeric gene codes for a protein of interest fused to the transcriptional activation domain of the transcriptional activator. Alternatively, the protein of interest may not be known and could be derived, for example, from a cDNA library. In a suitable host cell such as yeast, if the protein of interest and the bait protein do interact they bring into proximity the DNA-binding and transcriptional activation domains. This proximity is sufficient to cause transcription of a marker gene placed under the control of a promoter containing a binding site for the DNA-binding domain. Thus, the two-hybrid system generally allows detection of an interaction between two proteins by means of the positive signal of expression of a reporter gene.

Between plant species, e.g. monocotyledons, dicotyledons, and woody species, homologs typically have substantial sequence similarity, i.e. at least 75% sequence identity between nucleotide sequences. Sequence similarity is calculated based on a reference sequence, which may be a subset of a larger sequence, such as a conserved motif, coding region, or flanking region, for example. A reference sequence will usually be at least about 18 nucleotides (nt) long, more usually at least about 30 nt long, and may extend to the complete sequence that is being compared. Algorithms for sequence analysis are known in the art, such as BLAST, described in Altschul et al. *J. Mol. Biol.* 215: 403–410, 1990. The sequences provided herein are essential for recognizing BAS1 related and homologous proteins in database searches.

A "susceptible plant" refers to a plant that can be induced to utilize its endogenous bas1 gene to achieve overexpression of BAS1. The term "promoter inducing amount" refers to that amount of an agent necessary to elevate bas1 gene expression above bas1 gene expression in a plant cell not contacted with the agent. For example, a transcription factor or a chemical agent may be used to elevate gene expression from a bas1 native promoter, thus inducing or increasing the promoter and bas1 gene expression.

The gene tagging approach has been adopted in the studies presented herein to isolate activation tagging suppressors (ATS) of the missense mutation phyB-4. The phyB-4 mutation changes amino acid 283 from a histidine to a tyrosine. Studies of wildtype and mutant phyB protein expressed in yeast show that the phyB-4 mutation encodes a pigment capable of nearly normal phototransformation (T. D. Elich and J. Chory, *Plant Cell* 9:2271–2280, 1997). The phyB-4 mutant has a long hypocotyl in white light that is intermediate between the wild type and a null allele (M. Koornneef et al., *Heynh Z Pflanzenphysiol* 100S:147–160, 1980; J. W. Reed et al., *Plant Cell* 5:147–157, 1993). This weak phyB-mediated signal transduction "current" in the phyB-4 mutant makes it an ideal target for ATS analysis, allowing a broad based search of genes involved in developmental responses to light. This technique has resulted in a mutant identification of bas1-D (phytochrome B activation tagged suppressor1-dominant), caused by the amplified expression of the cytochrome P450: CYP72B1. The bas1-D enzyme catalyzes C26-hydroxylation of brassinolide, targeting it for inactivation. Transgenic lines with reduced expression of bas1-D have hypocotyls with enhanced responses to brassinolide and reduced responses to light. Crosses with photoreceptor null mutations place bas1-D downstream of phyA and cry1 generating a bypass suppressor of phyB alleles. We propose that the bas1-D gene acts as a control point between multiple photoreceptor signal transduction pathways and brassinosteroid signaling.

A bas1-D mutant *Arabidopsis* is a Dominant, Activation Tagged Suppressor of the phyB-4 Mutation Approximately 3000 phyB-4 T1 (primary transformant) transgenic seedlings containing T-DNAs with enhancer elements from the CaMV 35S promoter were screened for shorter hypocotyls in white light. From this screen, three dominant bas-D mutants were isolated that were caused by the amplified or over-expression of endogenous genes due to the proximal insertion of CaMV 35S promoter enhancer elements. The bas1-DphyB-4 double mutant exhibited a phenotype characterized by a significantly shorter hypocotyl than phyB-4 (FIGS. 2A–C). T3 seeds from heterozygotes in the T2 generation segregated 470 suppressed, kanamycin resistant plants and 147 non-suppressed, sensitive plants indicating that this transgene was located at a single locus. Southern analysis confirmed this conclusion. All of the kanamycin resistant plants conferred the bas1-DphyB-4 phenotype of short hypocotyls. In addition, all tall segregants were kanamycin sensitive, indicating that the tallness phenotype was linked to the bas1-DphyB-4 transgene. bas1-D homozygotes were indistinguishable from heterozygotes at the seedling stage, however, adult, heterozygous lines gave slightly better seed set.

Genomic DNA was cloned adjacent to the right border of the T-DNA by plasmid rescue (FIG. 2). BLAST searches (Altschul et al., supra) of flanking genomic DNA showed that the site of T-DNA insertion was on Chromosome II south of the ER marker at approximately 50 centimorgans on the physical map (See the sequenced and annotated bacterial artificial chromosome F18A8 (GenBank accession number: AC003105)). The four enhancer elements were inserted 381 nucleotides 5' to the start of the bas1 gene. Northern analysis of total RNA showed that this open-reading-frame was over-expressed in the bas1-DphyB-4 mutants. Two other predicted transcripts near the site of T-DNA insertion showed no altered accumulation in the bas1-DphyB-4 mutant. The overexpressed transcript encodes BAS1, a putative cytochrome P450 (CYP72B1). BAS1 is similar to clone T04442 in the *Arabidopsis* EST database (GenBank accession number: T04442)(T. Newman et al., *Plant Physiol.* 106:1241–1255, 1994). However, upon sequencing of the bas1 gene, an error in the sequencing of clone T04442 was discovered.

It was verified that bas1 encodes a complete cDNA for CYP72B1. phyB-4 mutant seedlings that were either transformed with the mutant gene in context with the CaMV enhancer elements or with the cDNA under the control of the CaMV 35S promoter recapitulated the original bas1-DphyB-4 phenotype as light-grown seedlings and adults, thereby demonstrating that overexpression of the bas1 gene is responsible for the bas1-DphyB-4 mutant phenotype.

The bas1-DphyB-4 double mutant resemble brassinosteroid mutants as light-grown seedlings and adults, showing that suppression of the phyB-4 long-hypocotyl phenotype is caused by the alteration of brassinosteroid synthesis or signaling. Unlike plants that lack or are insensitive to brassinosteroids, bas1-DphyB-4 seedlings did not have short hypocotyls in the dark. When recapitulation lines were grown in the dark, four out of five independent transformants with the cDNA under the control of the CaMV 35S promoter had short hypocotyls. Only one recapitulation line out of seven independent transformants with the bas1-D mutant clone had hypocotyls that were shorter than the original bas1-DphyB-4 mutant. This result indicates transcriptional regulation of this mutant gene. Northern analysis of the bas1-D transcript in the bas1-DphyB-4 mutant showed no difference in transcript accumulation between light and dark grown seedlings, suggesting that light does not regulate the overall accumulation of the bas1-D mRNA.

RT-PCR analysis demonstrated a difference in the accumulation of transcripts between rosettes and hypocotyls of phyB-4 and the bas1-DphyB-4 mutants, indicating tissue-specific transcriptional regulation for both the wildtype and mutant gene. As shown by quantification of RT-PCR products, there was a threefold higher accumulation of transcript in the rosette than in the hypocotyl in both phyB-4 and bas1-DphyB-4. In addition, the expression levels and patterns in the wild type were nearly identical to those in phyB-4. Quantification also showed that the overall accumulation of base transcript in bas1-DphyB-4 mutants was approximately 50 fold higher than in the phyB-4 mutant or in the wild type plant. This analysis of bas1 transcript accumulation taken together with the short hypocotyls found in dark-grown recapitulation lines demonstrates that bas1-D suppresses phyB-4 through the amplification of the endogenous bas1 expression pattern and not by the ectopic expression of this gene.

The three fold greater expression in the rosettes than in the hypocotyl is seen in both the wildtype, phyB-4 and the bas1-DphyB-4 mutant. However, even in the dark, though bas1-D has approximately a 50-fold greater expression than the wild type, only a slightly shorter hypocotyl was created, indicating that some light dependent mechanism causes hypocotyls of bas1-D mutants to become hyper-responsive to light. It remains to be seen it this control is transcriptional, post-transcriptional or translational.

Overexpression and Underexpression of CYP72B1 Confer Altered Responses to Brassinolide To test the role of the bas1 gene in wildtype plants, partial loss of function transgenic lines were generated via antisense constructs (D.C. Baulcombe, *Plant Mol Biol* 32:79–88, 1996). RT-PCR analysis showed that two of these lines exhibited approximately 50% of the wildtype bas1 transcript accumulation. These lines were epistatic to the dominant bas1-DphyB-4 mutant, further demonstrating that these are bonafide antisense mutants.

Figure 3:
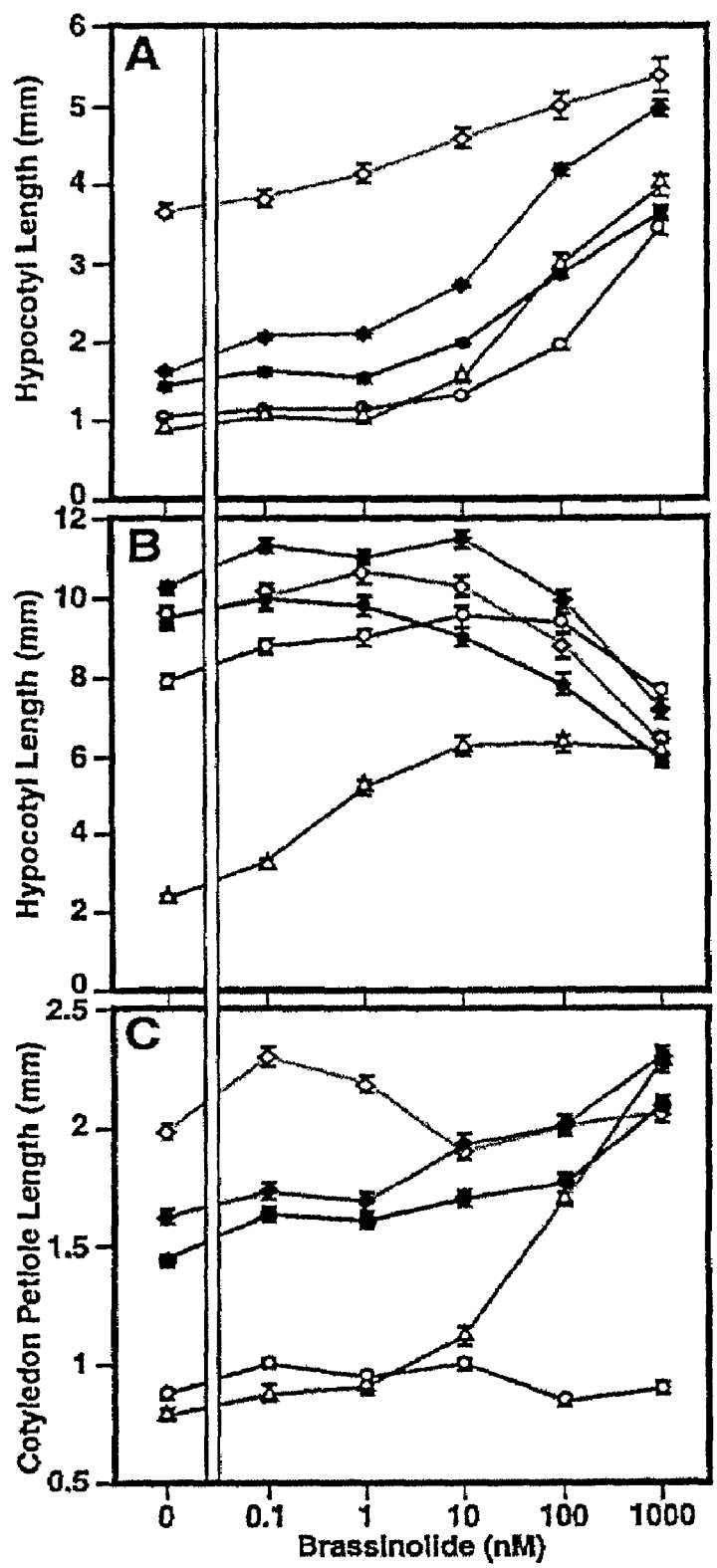
FIGS. 3A–C are graphs showing the dose response of hypocotyls of seedlings to brassinosteroid as measured after 6 days on varying levels of brassinolide.

Dose response experiments showed a hyper-responsivity to brassinolide for the hypocotyls of antisense lines when grown in the light (FIG. 3A) though not when grown in the dark (FIG. 3B). By contrast, a brassinosteroid biosynthesis mutant det2-1 produced petioles that were shorter than the wild type in the light, while the petioles of phyB-4 mutants were longer than the wild type in the light. In both cases, these phenotypes were rescued by exposure to increasing amounts of brassinosteroids. In contrast, the bas1-DphyB-4 mutant petioles were always shorter than the wildtype at all the brassinosteroid levels tested, indicating that, unlike det2-1, the rosette phenotype of bas1-DphyB-4 is insensitive to brassinosteroids (FIG. 3C).

Quantitative Analysis of Brassinosteroids in bas1-DphyB-4 and phyB-4

The overexpression of bas1 confers a dominant dwarf phenotype with rosettes that are insensitive to brassinolide (BR). To test whether the bas1-DphyB-4 gene inactivates or degrades brassinosteroids, endogenous levels of BRs from bas1-DphyB-4 and phyB-4 plants were determined by using gas chromatography-selected ion analysis with internal standards. The results of these studies (Table I) showed that castasterone and 6-deoxocastasterone were detected in bas1-DphyB-4, but at levels greatly reduced compared with those in phyB-4. Moreover, brassinolide was not detected in bas1-DphyB-4. Thus, endogenous levels of BRs in bas1-DphyB-4 were greatly diminished, indicating that this mutation affects BR levels and may be related to hydroxylation of brassinolide. In fact, an increased accumulation of 6-deoxoteasterone was found in the bas1-DphyB-4 mutant. Although the invention is not intended to be bound by mechanism, it is believed that this result could be caused by up-regulation of biosynthetic enzymes that are feedback-inhibited by an end-product brassinolide that was not detectable in the bas1-DphyB-4 mutant.

To test the hypothesis that overexpression of bas1 gene product results in hydroxylation of brassinolide, metabolism of deuterium-labeled and non-labeled brassinolide was examined using aseptically grown seedlings. As possible hydroxylated metabolites of brassinolide, 14-hydroxybrassinolide, 20-hydroxybrassinolide, 25-hydroxybrassinolide, 26-hydroxybrassinolide, and 28-hydroxybrassinolide were chemically synthesized. The possible hydroxylated brassinolide fractions from the feeding experiments were analyzed by gas chromatograph-mass spectrometry (GC-MS) after conversion to methaneboronate-trimethylsilyl derivatives.

In preliminary experiments, bas1-DphyB-4 and phyB-4 seedlings were fed $^2H_6$-labeled brassinolide (d6-BL) and incubated for one day. A prominent peak in GC-MS was found in bas1-DphyB-4 (the level was six times higher than in phyB-4 alone). Based on direct gas chromatography-mass spectrophotometry (GC-MS) comparison with authentic samples, it was suggested that the metabolite could be d6-BL hydroxylated at carbon 26 (d6-26-OHBL). To confirm the identification of 26-OHBL, experiments were performed with d6-brassinolide (d6-BL) and non-labeled-BL (BL). When BL was fed to the seedlings, 26-OHBL was detected as a metabolite of BL. The mass spectrum and retention time on GC were identical to those of authentic 26-OHBL. When d6-BL was fed to the seedlings, fragment ions such as m/z 625, 583 and 570 were detected. These fragment ions correspond to m/z 619, 577 and 564 of non-labeled 26-OHBL methaneboronate-trimethylsilyl derivative. Moreover, the retention time of the metabolite (i.e., the d6-26-OHBL derivative) on GC was one second earlier than that of non-labeled 26-OHBL derivative. This is due to an isotope effect. Thus, d6-26-OHBL was confirmed to be a metabolite of d6-BL. The level of this metabolite was five times higher in bas1-DphyB-4 than in phyB-4 mutants, demonstrating that brassinolide is converted to 26-hydroxybrassinolide in *Arabidopsis* seedlings, and that the conversion is greater in the bas1-DphyB-4 mutant.

Transcription of other BL Biosynthetic Cytochrome 450s in bas1-D Mutant

Brassinolide was not detected in the bas1-D mutant (Table I). Through feedback regulation, this may cause certain brassinosteroid biosynthetic enzymes to have altered expression in a bas1-D mutant background. CYP90A1 (encoded by the cpd gene) (M. Szekeres et al., *Cell* 85:171–182, 1996) transcript accumulates less in plants fed brassinolide (J. Mathur et al., *Plant J* 14:593–602, 1998). Transcript accumulation of CYP90A1 and its family member CYP90B1 (encoded by the dwf4 gene) (S. Choe et al., *Plant Cell* 10:231–43, 1998) was examined in bas1-DphyB-4 mutant plants, in wild type plants, and in both bas1 antisense lines. Both cpd and dwf4 transcripts accumulated five-fold more in the bas1-DphyB-4 mutant than in the wild type plant, demonstrating that both of these genes confer altered expression in the bas1-DphyB-4 mutant. Unlike cpd, the dwf4 transcript accumulated 50% less in the bas1 antisense lines than in wild type plants.

Fluence Response Analysis

Figure 4:
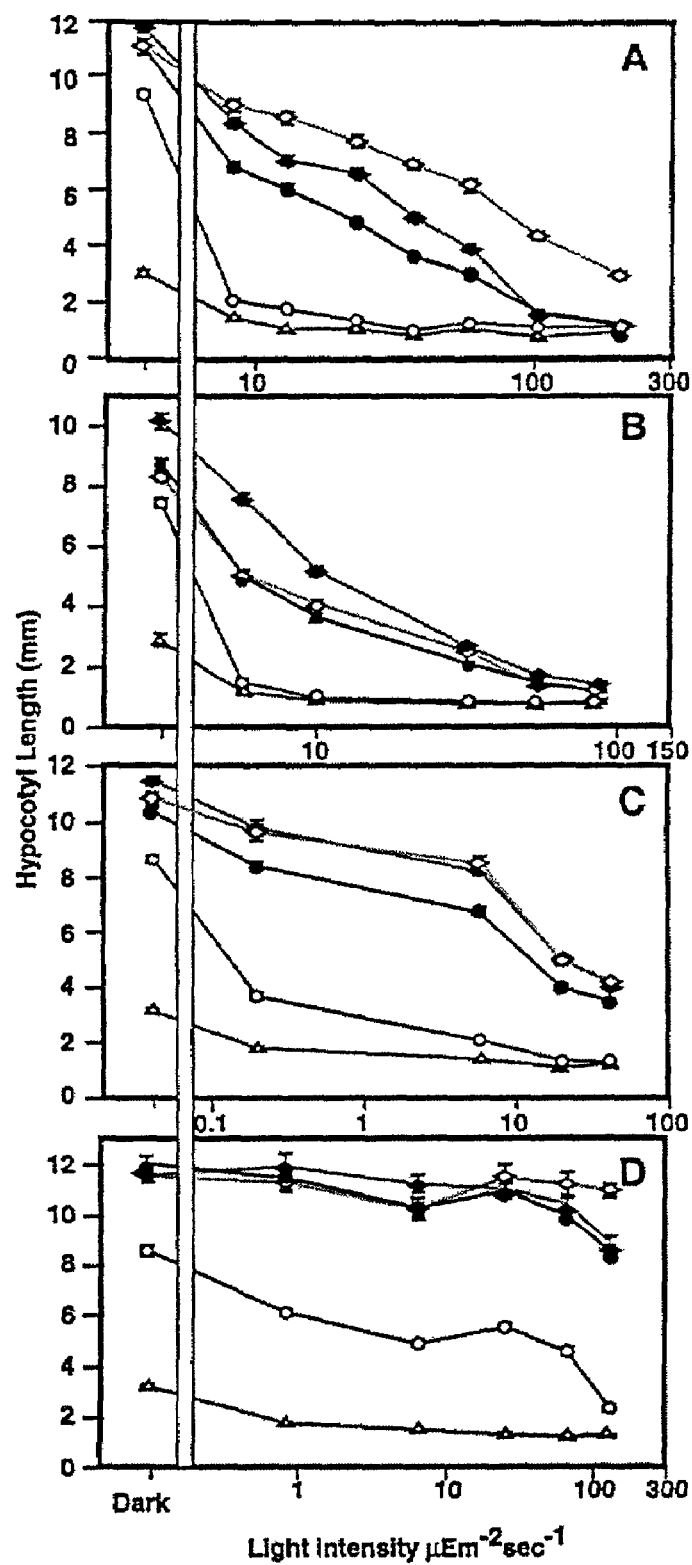
FIGS. 4A–D are graphs showing light fluence response of hypocotyls of six-day old seedlings measured after growth in the dark or in varying intensities of light.

To test the role of bas1 gene in light signal transduction, the response of both overexpressors and underexpressors of bas1 was analyzed in varying qualities and quantities of light. Though the bas1-DphyB-4 mutant was slightly shorter than the wild type in the dark, it was hyper-responsive to continuous white, red, far-red and blue light. By contrast, the bas1 antisense lines had hypocotyls that were slightly longer than the wild type in the dark, showed a reduced responsiveness to white, far-red and blue light (FIGS. 4A–C), and exhibited a wildtype response to red light FIG. 4D). As expected, phyB-4 mutants had a reduced response to white light and red light as compared to the wild type. It is likely that there is minimal bas1 activity downstream of red light since the bas1-DphyB-4 mutant was less responsive to red light than to the other light conditions while the bas1 antisense lines responded normally to red light.

Figure 5:
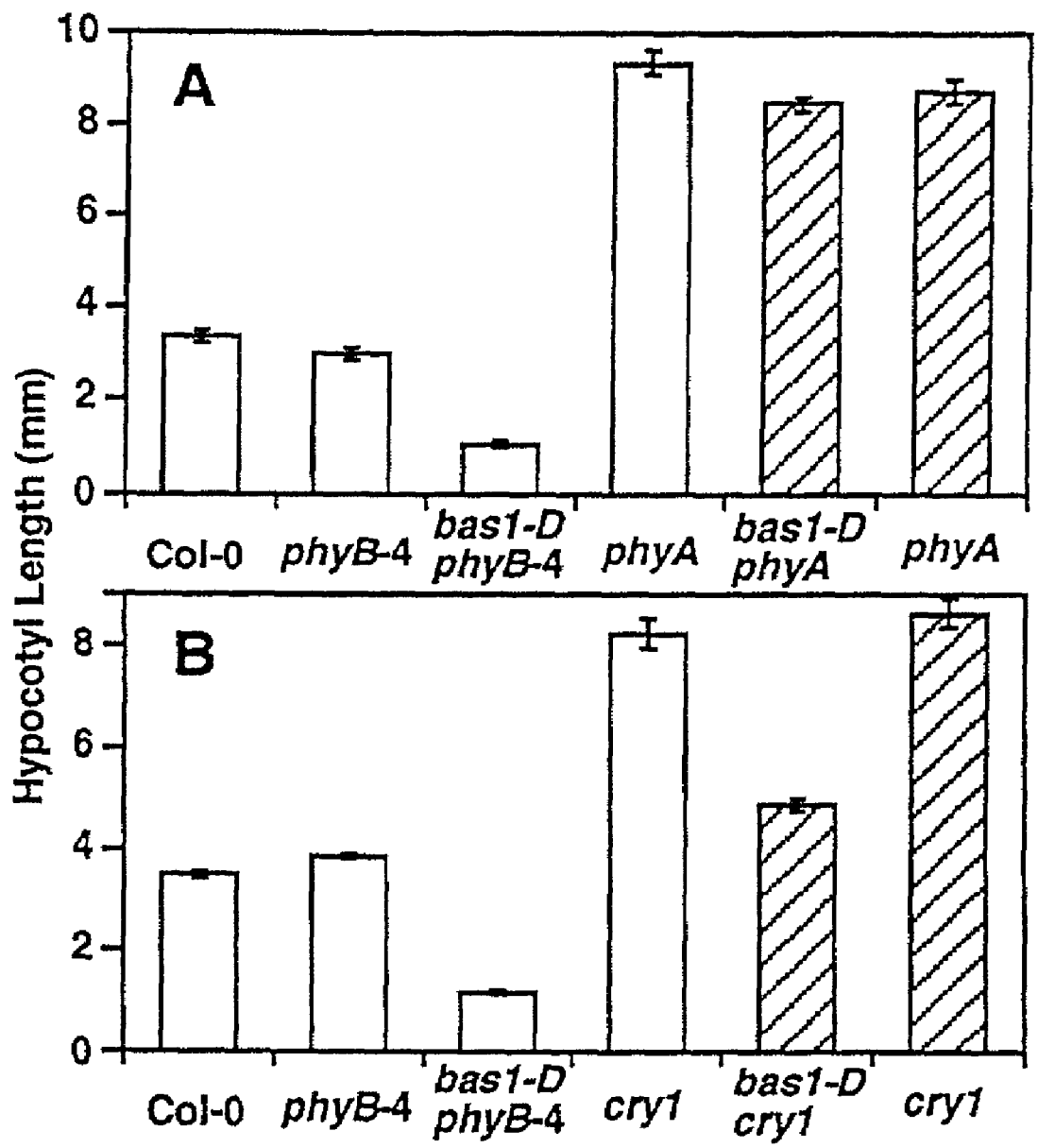
FIGS. 5A and 5B are graphs showing the results of segregation analysis of double mutants.

To test which of the photoreceptors controls the activity of bas1, double mutants were made with bas1-D and null alleles of phyA, phyB, and cry1 (FIGS. 5A–B). In continuous far-red light, bas1-D did not suppress a phyA null mutation (FIG. 5A). In continuous blue light, bas1-D partially suppressed a cry1 null mutation (FIG. 5B). In contrast, bas1-D fully suppressed a phyB null mutation. Taken together with the fluence response analysis (FIGS. 4A–D), these data indicate that in bas1-D mutants (which overexpress the bas1 gene) phyB alleles are suppressed through the activity of at least phyA and cry1 and can be formally placed as a bypass suppressor of phyB.

Heterologous Expression

To test whether the *Arabidopsis thalia* bas1 gene is active in an heterologous system, tobacco plants were transformed with either the bas1-D mutant gene or bas1 cDNA being driven by the CaMV 35S promoter (See Example 11 herein). In both cases, it was possible to create dwarf tobacco plants having a phenotype reminiscent of that created in the original bas1-DphyB-4 mutant in *Arabidopsis*. Tobacco plants expressing the bas1-D mutant gene had dark-green, epinastic leaves with short stems and petioles when compared to the wild type. Dark grown seedlings from these plants had hypocotyls that were similar to the wild type in the dark, the more severe of the two having slightly shorter hypocotyls reminiscent of dark grown bas1-DphyB-4 mutants.

Transgenic tobacco plants expressing the bas1 cDNA under control of the CaMV 35S promoter also demonstrated the attributes of light grown dwarfs. When these seedlings were grown in the dark, they had significantly shorter hypocotyls than the wild type, with the weaker of the two cDNA expressors having dramatically shorter hypocotyls than the strongest of the two lines expressing the bas1-D mutant gene. These results indicate that brassinosteroids can be inactivated by CYP72B1, the product of the bas1 gene, in tobacco and that there is a similar transcriptional control of bas1 gene expression in this heterologous plant systems.

bas1-D Suppresses the phyB-4 Mutation Through the Inactivation of Brassinosteroids The identification of bas1-D gives significant insight into two complex signaling processes and how these processes interact to regulate plant development. The interplay between light and hormone signaling has been studied for years though mechanisms between these pathways are poorly understood. Enhanced expression (i.e., overexpression of CYP72B1 suppresses the long hypocotyl phenotype of the weak photoreceptor mutant phyB-4. The results of studies described above indicate that this enzyme catalyzes brassinosteroid inactivation via hydroxylation given that: the bas1-DphyB-4 mutant resembles brassinosteroid mutants; there is no detectable brassinolide in the bas1-DphyB-4 mutant; and the bas1-DphyB-4 mutant converts brassinolide to a C26-hydroxylated form at a greater rate than the wildtype. Feeding and dose response experiments argue that one of the substrates for CYP72B1 is the biosynthesis end product brassinolide. However, measurements of brassinolide biosynthesis precursors show reduced levels of both castasterone and 6-deoxocastasterone in the bas1-DphyB-4 double mutant compared to phyB-4 alone, suggesting that CYP72B1 can also act on brassinosteroid precursors.

The accumulation of 6-deoxoteasterone in bas1-DphyB-4 is probably caused by increased activity of the steroid hydroxylases CYP90A1 catalyzing the C-23 hydroxylation of (6-deoxo)cathasterone to (6-deoxo)teasterone, originally identified as the loss-of-function alleles cpd, dwf3 and cbb3 (M. Szekeres et al., supra; A. Kauschmann et al., *Plant J.* 9:701–713, 1996). The cpd gene is expressed in the cotyledons and young leaves of developing seedlings and is down-regulated by brassinolide (Mathur et al., supra). Since brassinolide is not detectable in rosettes of bas1-DphyB-4, one would expect the observed higher expression of cpd in rosettes. CYP90B1, a family member with CYP90A1 and originally identified as the dwf4 allele (Choe et al., supra), catalyzes the C-22 hydroxylation step prior to cpd activity. CYP90B1 also has increased transcript accumulation in the bas1-DphyB-4 mutant. DWF4 transcripts accumulate roughly 50% in BAS1 antisense lines when compared to the wild type, correlating nicely with the BAS1 transcript accumulation in these lines and arguing that DWF4 transcription in tightly regulated by the brassinolide biosynthesis pathway. The accumulation of 6-deoxoteasterone in bas1-DphyB-4 mutants gives sufficient biochemical evidence to say that BAS1 does not efficiently hydroxylate 6-deoxoteasterone, acting downstream of this intermediate in brassinolide biosynthesis (most likely on multiple intermediates in addition to brassinolide). This conclusion genetically places BAS1 downstream of both CPD and DWF4. That there is an accumulation of 6-deoxoteasterone in the bas1-DphyB-4 mutant also argues that BAS1 activity is likely to be one of the rate-limiting steps in brassinosteroid biosynthesis in leaves.

A putative brassinosteroid receptor, BRI1, has been cloned and shown to have homology with leucine-rich repeat receptor kinases (Li and Chory, supra). Unlike the brassinosteroid biosynthesis mutants, loss-of-function bri1 alleles are insensitive to brassinolide applications, identifying them as signaling mutants. The nature of the gene product suggests that bri1 encodes the brassinolide receptor; however, brassinosteroid binding by BRI1 has not been shown. One of the perplexing aspects of involvement of BRI1 in brassinolide perception is that the gene seems to be ubiquitously and constitutively expressed throughout *Arabidopsis* growth and is not regulated by light, a pattern that is similar to expression of the brassinosteroid biosynthetic gene DET2 (Li and Chory, supra). This finding raises the question of how brassinosteroids act as hormones if they are metabolized and perceived in the same cell. One way of regulating tissue specific responses to brassinolide is by inactivation of the steroid through BAS1 mediated hydroxylation. That BAS1 has tissue-specific transcriptional regulation supports this model. Both gain-of-function and loss-of-function bas1 mutations confer altered brassinosteroid responses in light-grown hypocotyls, arguing that in this tissue the activity of CYP72B1 determines the degree of response to brassinosteroids. Though dark-grown bas1-DphyB-4 seedlings are etiolated, they have hypocotyls that are slightly shorter than the wildtype. In addition, dark-grown bas1 antisense lines have slightly longer hypocotyls than the wild type. These results argue that it is the activity of CYP72B1 that ultimately controls the hypocotyl response to brassinosteroids.

Hormone inactivation by hydroxylation is a mechanism shared by plant and insect systems. As is the case with BAS1, a cytochrome P450 (CYP450)-mediated C26-hydroxylation inactivates the insect hormones, ecdysteroids (H. H. Rees, *Eur. J. Entomol.* 92:9–39. 1995; H. Kayser et al., *Eur J Biochem* 248:707–16, 1997; D. R. Williams et al., *J. Biol Chem* 272:8427–32,1997). Though ecdysteroids are inactivated in a similar manner to brassinosteroids, these insect hormones do not induce brassinosteroid responses in plants (S. D. Clouse et al., *Plant Physiol* 100:1377–1383, 1992). Other insect juvenile hormones can be hydroxylated and presumably catabolized in a similar manner to ecdysone (T. D. Sutherland et al., *Proc Natl Acad Sci USA* 95:12884–9, 1998). CYP450-dependent C24-hydroxylation of 1α,25-dihydroxyvitamin D-3 inactivates this form of vitamin D in both rats (C. Hahn et al., *Nucleic Acids Res* 22:2410–6, 1994; R. Kumar et al., *J Biol Chem* 253:3804–9, 1978) and humans (K. S. Chen et al., *Biochim Biophys Acta* 1263:1–9, 1995). In plants, 2β-hydroxylation inactivates gibberellins, targeting them for destruction. There are at least two CYP450s that catalyze this reaction in pea (Lester et al., *Plant J* 19:65–73, 1999) and at least three in *Arabidopsis* (Thomas et al., supra). In both cases, there appears to be some genetic redundancy with overlapping as well as distinct transcriptional patterns in different tissues. Given the genetic redundancy of gibberellin 2β-hydroxylases in pea and *Arabidopsis* a similar genetic redundancy may be present for hydroxylation mediated inactivation of brassinosteroids.

Hormone inactivation by hydroxylation is not an uncommon mechanism. As is the case with BAS1, CYP450-mediated C26-hydroxylation inactivates the insect hormones ecdysteroids (Rees, supra; Kayser et al., supra; Williams et al., supra). Though ecdysteroids are inactivated in a similar manner to brassinosteroids, these insect hormones do not induce brassinosteroid responses in plants (Clouse et al., supra). Other insect juvenile hormones can be hydroxylated and presumably catabolized in a similar manner to ecdysone (Sutherland et al., supra). CYP450-dependent C24-hydroxylation of 1α,25-dihydroxyvitamin D-3 inactivates this form of vitamin D in both rats (Hahn et al., supra; Kumar et al., supra) and humans (Chen and DeLuca, supra). In plants, 2β-hydroxylation inactivates gibberellins, targeting them for destruction. There are at least two CYP450s that catalyze this reaction in pea (Lester et al., supra) and at least three in *Arabidopsis* (Thomas et al., supra). In both cases, there appears to be some genetic redundancy with overlapping as well as distinct transcriptional patterns in different tissues. Given the genetic redundancy of gibberellin 2β-hydroxylases in pea and *Arabidopsis* a similar genetic redundancy may be present for hydroxylation mediated inactivation of brassinosteroids.

There is at least one other CYP72 in *Arabidopsis* (chibi2) that when overexpressed confers a brassinosteroid-minus phenotype similar to bas1-D mutants. Given the genetic redundancy in this brassinolide catabolic process, it is not surprising that bas1-D and chibi2 were both isolated in gain-of-function mutant screens. C26-hydroxylation is probably not the only pathway for inactivating brassinosteroids. Steroid sulfotransferases have been isolated from both *Brassica napus* and *Arabidopsis* and shown to inactivate brassinolides through O-sulfonation (M. Rouleau et al., *J Biol Chem* 274:20925–30, 1999). Though an in vivo role for these sulfotransferases has yet to be determined, it is clear that there are multiple mechanisms for the control of brassinosteroids through their catabolism.

Since the bas1-D mutation is caused by a gain-of-gene-function mutation, the bas1-D mutation can be transferred into heterologous plant systems. It has been shown that use of the bas1-D or the bas1 cDNA fused to the CaMV 35S promoter creates brassinosteroid minus mutants in tobacco where no such mutants exist. To date, the only way to study tobacco plants lacking brassinolide is to grow them on the brassinosteroid biosynthesis inhibitor brassinazol (T. Asami and S. Yoshida, S., *Trends Plant Sci* 4:348–353, 1999). Tobacco plants grown on high levels of brassinazol look similar to weak transgenic lines with enhanced expression of bas1. There are multiple advantages to using plants overexpressing bas1 to replace growth of plants on brassinazol to study brassinosteroid function in a variety of plant types. Depending on the transgene used, the dark grown phenotype of transgenic lines can be controlled in plants overexpressing bas1. The transgenic plants confer a gain-of-function allelic series, similar to and even more severe than plants grown on increasing levels of brassinazol. By using this allelic series in future experiments, the need to do a brassinazol dose response under different environmental conditions can be avoided. For example, such an allelic series can be used to address the fitness of individuals with different steady state levels of active brassinolides under natural selection permitting the role of brassinosteroids to be addressed in plants less amenable to genetic analysis than *Arabidopsis*. In addition, transgenic tobacco lines that overexpress bas1 may facilitate further biochemical analysis because large amounts of tobacco tissue are easier to obtain than is *Arabidopsis*.

The studies presented in the Examples herein represent the first example of activation tagging suppression analysis in *Arabidopsis*. By searching for ATS alleles targeting phyB-4, a control point has been identified between multiple light-signaling pathways and brassinosteroid biosynthesis/sensing. Further, a cytochrome P 450 (CYP450) has been identified that most likely catalyzes the C-26 hydroxylation and subsequent inactivation of brassinolide. Genetic analysis places this activity down stream of multiple photoreceptors. Therefore, it is believed this CYP72B1 acts as a major control point in the catabolism of brassinosteroids, regulating responses to this hormone in different tissues of the developing seedling. We have also expressed the CYP72B1 gene in tobacco, creating the first example of brassinosteroid mutants in this species. Given the genetic strengths of *Arabidopsis* as a model system, ATS analysis should become a major genetic approach to further understanding developmental processes in plants.

The above disclosure generally describes the present invention. A more complete understanding can be obtained by reference to the following specific examples which are provided herein for purposes of illustration only and are not intended to limit the scope of the invention.

EXAMPLE 1

Mutant Screen

The bas1-DphyB-4 mutant was identified as having a shorter hypocotyl than phyB-4 in the following screen. The phyB-4 mutation was originally isolated in the La-er genetic background (M. Koornneef et al., supra; J. W. Reed et al., 1993, supra). To improve transformation efficiency, this mutation was introgressed into the Col-0 genetic background six times. Polymorphic markers between La-er and Col-0 were used to identify lines that were introgressed into the Col-0 background (C. Konieczny and F. M. Ausubel, *Plant J.* 4:403–410, 1993). phyB-4 mutants were transformed with the activation-tagging construct pSKI074 that contains four copies of enhancer elements from the CaMV 35S promoter. This construct was modified from the plasmid pPCVICEn4HPT where the hygromycin resistance gene was exchanged with neomycin phosphotransferase gene, which confer resistance to the antibiotic kanamycin (Igor Kardailsky, Detlef Weigel per. comm.) Kanamycin resistance was preferred as a genetic marker for the transgene because the hypocotyl phenotype of phyB-4 was easily scored on this selection media. Plants were transformed with the floral dip technique (S. J. Clough and A. F. Bent, *Science* 282:1698–701, 1998). The *Agrobacterium* strain used was GV3101.

Seeds were sterilized by first shaking in 70% (v/v) EtOH with 0.05% (v/v) Triton X-100 for 15 minutes then in 95% (v/v) EtOH for 15 minutes. Sterile seeds were placed on sterile Whatman filter paper in a laminar air flow hood and allowed to dry before being sprinkled onto standard growth media (D. Valvekens et al., *Proc. Nat. Acad. Sci. USA* 85:5536–5540, 1988; Neff and Chory, supra) with 30 μg/L of kanamycin at a density of approximately 2000 seeds per 150 mm ×20 petri dish. In all experiments, plates with kanamycin (30 μg/L) or gentamycin (60 μg/L) used 0.8% phytagar (GibcoBRL Life Technologies, Grand Island N.Y.) as a gelling agent and those without selection used 1.0% phytagel (Sigma Chemical Co., St. Louis, Mo.). After a four day dark treatment at 4° C., seedlings were grown for six days at 20° C. in 150 $\mu Em^{-2}s^{-1}$ of continuos white light supplied by six HO-CW fluorescent tubes (GE lighting, Cleveland, Ohio) and two 25-W incandescent bulbs in a plant growth chamber (model E30B Percival Scientific, Boone, Iowa). Putative suppressors having shorter hypocotyls than phyB-4 were analyzed for the phyB-4 mutation by PCR amplification with the following gene specific primers:

5'- CTGTCGTGGAAAGTGTGAGG -3' (SEQ ID NO:4) and

5'- GAACCTTGACGCTTGAGG -3' (SEQ ID NO:5)

The PCR products were resolved on a 2.5% MetaPhor agarose gel (FMC BioProducts, Rockland, Me.) after digestion with the restriction endonuclease Nla III. Minipreps of plant genomic DNA and PCR conditions are described in (Neff et al., *Plant J.* 14:387–392, 1998).

EXAMPLE 2

Cloning and Molecular Analysis

Since the bas screen was performed on primary (T1) transformants, a screen was used that specifically selects for dominant or semidominant mutants. The original bas1-DphyB-4 mutant was allowed to self pollinate, and T2 seeds were rescreened on plates with and without kanamycin selection. This showed that the suppression phenotype bred true and that the original mutant was indeed a dominant allele caused by the insertion of the transgene at a single locus.

T2 seeds were also germinated in the dark and had a deetiolation phenotype similar to the wild type indicating that this suppression was not caused by a general cell elongation defect. 35 T2 plants were grown and rescreened again on plates with and without kanamycin. All plants that were scored as non-suppressing in the previous generation bred all long and kanamycin sensitive seedlings in the T2 generation. All homozygous suppressor lines were 100% kanamycin resistant. Heterozygous lines again segregated as dominant alleles with kanamycin sensitive plants being long and non-suppressing. As a result, we established linkage of the transgene to less than 3 centimorgans of the suppression mutation.

EXAMPLE 3

Southern Analysis, Plasmid Rescue, and cDNA Sequencing

Plant DNA was prepared from 1–2 grams (fresh weight) of homozygous bas1-DphyB-4 and phyB-4 lines using the PhytoPure plant DNA extraction kit (Nucleon Biosciences, UK). Plant DNA was digested with the restriction endonucleases EcoR I, Xho I, Hind III, Kpn I, Not I, and BamH I. DNA was electrophoresed on a 0.7% agarose gel in 1X TAE, transferred to Hybond N+using the recommended alkaline transfer method (Amersham, LifeScience UK), hybridized with $^{32}$P-radiolabeled pBlueScript (Stratagene, La Jolla Calif. USA), washed and exposed for one day on X-ray film (Eastman Kodak Co. Rochester N.Y.). From this it was determined that the bas1-DphyB-4 mutant had a single, simple T-DNA insertion which could be used for plasmid rescue from the right border. After several phenol extractions, 2 μg of total bas1-DphyB-4 DNA digested with Hind III or Kpn I was ligated overnight in a total volume of 250 μL. The ligase solution was EtOH precipitated, resuspended in 12 μL of $dH_2O$ and 3 μL was used for electroporation into Epicurian Coli® SURE® 2 supercompetent cells (Stratagene, La Jolla Calif. USA). These cells were used because of their low frequency of recombination with unstable DNA such as the four, in tandem, copies of enhancer elements. The 7.3 kb Hind III rescued plasmid (pBAS1H) was sequenced with a primer 3' of the Hind III site in the T-DNA (5' GCTCTCTCGAGGTCGACGG 3'). (SEQ. ID NO: 6) A BLAST search (Altschul et al., supra) resulted in an exact hit on genomic sequence encoding CYP72B1 and the EST T04442. The PCR primer (5' GCTTGCTGGAC-TATTTGAGC 3')(SEQ ID NO: 7) and T7 primer sequence were used to amplify the junction of insertion in the bas1-DphyB-4 mutant and the two rescued plasmids, thus showing that all three shared the same architecture of insertion and that all four copies of the enhancer elements were intact. The Kpn I rescued plasmid (pBAS1K) was 13.67 kb and contained the entire gene encoding CYP72B1 plus 6.33 kb of genomic sequence 3' of the CYP72B1 open reading frame.

The EST T04442 was sequenced and shown to be a complete cDNA encoding the CYP72B1 gene. An error was founds in the database entry for the sequence from BAC F18A8 where nucleotide 784 of this cDNA sequence was a C instead of the reported T. Thus, amino acid 262 was annotated as a tryptophan instead of the correct arginine. The corrected DNA sequence encoded a recognition site for the restriction endonuclease BsmA I. We confirmed the presence of this restriction site by PCR amplification, digestion and resolution using the cDNA, the BAC F18A8, or genomic DNA from Col-0, phyB-4 and bas1-DphyB-4 as templates (data not shown).

EXAMPLE 4

Northern Analysis

Eight-day old seedlings were quickly harvested from the plates prepared as described in Example 2 and frozen in liquid nitrogen, then stored at −80° C. until used. 200 mg of frozen seedlings were ground up in liquid nitrogen along with 0.5 ml of RNA extraction buffer (100 mM NaCl, 10 mM Tris pH 7.5, 1 mM EDTA, 1% SDS), and 150 μL phenol. The powder mix was extracted with 300 μl chloroform and precipitated overnight with an equal volume of 4M LiCl. The pellet was resuspended in 300 μl of diethyl phosphorocyanidate (DEPC) treated water. After the addition of 33 μl of 3M NaOAc (pH 5.2) and 830 μl of EtOH a 1 hour treatment of −20° C. and centrifugation was used to pellet total RNA. For northern analysis, 10 μg of RNA was loaded on 1.3% formaldehyde-containing agarose gel and electrophoresed in 1×3-(N-morpholineo)-propane sulphonic acid (MOPS) buffer (20 mM MOPS, 5 mM NaOAc, 1 mM ethylene diamine tetraacetic acid (EDTA)) followed by transfer to a Hybond-NX nylon membrane for 18 hours as recommended (Amersham, UK). After transfer, RNA was fixed to the membrane by baking at 80° C. for 1 hour. A PCR product of the CYP72B1 cDNA was used as a probe and treated the same as in the southern analysis.

EXAMPLE 5

RT-PCR Analysis

Tissue from wild type and antisense lines were grown for nine days in 150 μEm$^{-2}$s$^{-1}$ of continuous white light before being harvested in liquid N$_2$ and stored at −80° C. For the hypocotyl vs. rosette RT-PCR analysis, seedlings were grown for 5 days in the dark (to induce hypocotyl growth) then 9 more days in 150 μEm$^{-2}$s$^{-1}$ of continuous white light. Rosette and hypocotyl tissue was collected and frozen immediately in liquid N$_2$ before being stored at 80° C. Total RNA was isolated using TRIzol®Reagent as recommended by the manufacturer (GibcoBRL Life Technologies, Grand Island N.Y.). cDNAs from 1 μg of total RNA were synthesized using 500 ng of a 27-mer oligo-dT and the reverse transcriptase SuperScript™ (GibcoBRL Life Technologies, Grand Island N.Y.). One tenth of the cDNA reaction was used for each PCR (see (Neff et al., supra, which is incorporated herein by reference in its entirety) for conditions). Primers spanning the third intron of BAS1 were used to detect this transcript (5'-GGTTCAGGACATTGTGGAGG-3' (SEQ ID NO:8) and 5'-GGATACAACCTTAAA-GACTCG-3' (SEQ ID NO:9)). Primers spanning the last intron of CPD were used to detect this transcript (5'-GCAACTCGGTAACGACAGGC -3' (SEQ ID NO:10) and 5'-TCAAGTAGCAAAATCACGGCG-3' (SEQ ID NO:11)). Primers spanning the last intron of DWF4 were used to detect this transcript (5'-CTCTTTAATCCTTG-GAGATGGC-3' (SEQ. ID NO:12) and 5'-GGTTGAT-CATCTTCTGCTAATTCCC-3' (SEQ ID NO:13)). Primers amplifying the UBQ10 gene were used as a control for total template concentration (5'-GATCTTTGCCGGAAAA-CAATTGGAGGATGGT-3' (SEQ ID NO:14) and 5'-CGACTTGTCATTAGAAAGAAAGAGATAACAGG-3' (SEQ ID NO: 15)). Products from PCR runs with varying numbers of cycles were electrophoresed and probed followed by quantification using a phosphoimager (Molecular Dynamics). Phosphoimager analysis on varying numbers of PCR cycles showed that the RT-PCR results presented were within the linear range of accuracy.

As shown by quantification of RT-PCR products, there was a threefold higher accumulation of transcript in the rosette than in the hypocotyl in both phyB-4 and bas1-DphyB-4. In addition, the expression levels and patterns in the wild type were nearly identical to those in phyB-4. Quantification also showed that the overall accumulation of bas1 transcript in bas1-DphyB-4 mutants was approximately 50 fold higher than in the phyB-4 mutant or in the wild type plant. This analysis of bas1 transcript accumulation.

EXAMPLE 6

Recapitulation and Antisense Constructs

Two types of constructs were used for recapitulation of the bas1-D mutant phenotype. The first contained the BAS1-D genomic clone of the bas1-D mutant gene from the pBAS1K rescued plasmid. After restriction of pBAS1K with the endonucleases BamH I and Sac I, a 5.7 kb fragment containing the entire CYP72B1 open reading frame in the context of the four enhancer elements was cloned into the binary vector pPZP212 (Hajdukiewicz et al., *Plant Cell* 9:1951–1962, 1997 1994). The second, containing the cDNA under the expression of the CaMV 35S promoter, was made by cloning either a BamH I/Sal I fragment or a BamH I/Kpn I fragment from the T04442 cDNA clone into the binary vector pCHF3, which contains the CaMV 35S full promoter, the RBCS terminator from pea, and confers kanamycin resistance for selection in plants. A construct constitutively expressing BAS1 antisense RNA was made by cloning a BamH I/Sac I fragment into the binary vector pCHF1, which contains the CaMV 35S full promoter, the RBCS terminator from pea, and confers gentamycin resistance for selection in plants.

Dose response experiments showed a hyper-responsivity to brassinolide for the hypocotyls of antisense lines when grown in the light though not when grown in the dark. By contrast, a brassinosteroid biosynthesis mutant det2-1 produced petioles that were shorter than the wild type in the light, while the petioles of phyB-4 mutants were longer than the wild type in the light. In both cases, these phenotypes were rescued by exposure to increasing amounts of brassinosteroids. In contrast, the bas1-DphyB-4 mutant petioles were always shorter than the wildtype at all the brassinosteroid levels tested, indicating that, unlike det2-1, the rosette phenotype of bas1-DphyB-4 is insensitive to brassinosteroids.

EXAMPLE 7

Dark Grown Recapitulation Seedlings

To examine the dark-grown phenotype of bas1-D recapitulation lines, T2 seedlings were grown for 6 days in the dark on standard growth media without antibiotic selection. These seedlings were transferred under sterile conditions to growth media with kanamycin selection, laid flat on the agar and were imaged with a flat bed scanner (Neff and Chory, supra). After scanning, seedlings were grown for one week in continuous white light to score for resistance to kanamycin. The dark-grown hypocotyl length was determined from the digital image of seedlings determined to be kanamycin resistance. In each case, seedlings determined to harbor the transgene, developed a rosette phenotype similar to bas1-DphyB-4. Tobacco seedlings were treated in a similar manner.

These studies showed that dark-grown bas1-DphyB-4 seedlings are etiolated, but have hypocotyls that are slightly shorter than the wildtype. In addition, dark-grown bas1 antisense lines have slightly longer hypocotyls than the wild type. These results argue that it is the activity of CYP72B1 that ultimately controls the hypocotyl response to brassinosteroids.

EXAMPLE 8

Genetic Analysis with Photoreceptor Null Mutants

For analysis of interactions between bas1-D and different photoreceptors, bas1-DphyB-4 plants were crossed with the null photoreceptor mutants, phyB-5, phyA-201 and hy4-2.23N(cry1). F2 seeds were grown on standard growth media with 30 μg/L of kanamycin. For the bas1-DphyB-4phyA-201 mutant, F2 plants, that had long hypocotyls after six days in far-red light and conferred kanamycin resistance upon subsequent growth in white light, were genotyped for the phyB-4 and phyA-201 mutations (Neff et al., supra). For the bas1-DphyB-4cry1 mutant, F2 plants that had longer hypocotyls after six days in blue light and conferred kanamycin resistance upon subsequent growth in white light were genotyped for the phyB-4 and cry1 mutations (Neff and Chory, supra). Since bas1-DphyB-4 was isolated in a Col-0 ecotype background and the phya and cry1 mutants were isolated in the La-er ecotype, F3 populations were examined that were homozygous for phyB-4 and phyA or cry1 yet segregated the bas1-D mutation. This allowed testing of the effect these photoreceptors had in the presence or absence of the bas1-D mutation while controlling for variations caused by the different ecotypes. To test the effect of the bas1-D mutation in a phyB null mutant background, F3 seeds were grown from a line that was heterozygous for bas1-D and segregated phyB-5/phyB-4. More than 200 F3 seedlings were examined, but no plants were found that had both long hypocotyls and conferred kanamycin resistance in white light, showing that bas1-D did suppress a phyB null mutation.

EXAMPLE 9

Brassinolide Dose Response and Light Conditions (CIDtech Research Inc., Mississauga, Ontario, Canada) 2 mM Brassinolide stock was made by dissolving in 95% (v/v) EtOH and stored at −20° C. The 1 μM solution was made by a 1:2000 fold dilution of the 2 mM stock in standard growth media. All other concentrations including the negative control contained the same amount of EtOH. Light conditions for fluence responses in red and blue light and seedling measurements were performed as described in Neff and Chory, supra. An E30LED growth chamber (Percival Scientific, Boone, Iowa) supplied far-red light. Far-red fluences were measured with a portable spectroradiometer (model LI-1 800, Li-Cor, Inc., Lincoln, Nebr.).

EXAMPLE 10

Biochemical Analysis

For brassinosteroid measurements, plants were grown on soil (Neff and Chory, supra) in short day conditions (8 hours of light, 18 hours of dark) for five weeks before rosettes were harvested in liquid nitrogen. No visible floral bolts were seen at this time. Tissue was stored at −80° C. prior to lyophylization. 200 grams fresh weight of phyB-4 and 100 grams fresh weight of bas1-DphyB-4 were collected. Brassinosteroids were analyzed according to the methods described by (S. Fujioka et al., *Plant Cell* 9:1951–1962, 1997). Before feeding experiments, seven day old seedlings were transferred to a 200-mL flask containing 30 mL of growth media without agar and supplemented with 1% sucrose (phyB-4, 50 seedlings; bas1-DphyB-4, 100 seedlings). Five days after transfer, an EtOH solution (50 mL) of $^2H_6$-labeled brassinolide (50 mg) or non-labeled brassinolide (50 mg) was added to a 200-mL flask containing *Arabidopsis* seedlings. The seedlings were incubated for one day at 22° C. in the light on a shaker (125 rpm). After incubation, the seedlings were extracted with MeOH. The MeOH extract was purified with a cartridge of silica gel (Sep-Pak Vac 2g; Waters, Milford, Mass.), which was eluted with 30 mL of chloroform, 3% MeOH in chloroform, and 20% MeOH in chloroform. The last fraction was purified with HPLC on a 150-×4.6-mm Senshu Pak ODS-1 151-D column (Senshu Scientific Co., Ltd., Tokyo) by using 45% acetonitrile at flow rate of 1.0 mL/min. The fractions were collected every one min. (retention time of 1 to 10 min.).

Each fraction was subjected to GC-MS analysis after derivatization. 26-OHBL was detected from retention time of 2–3 min. Authentic hydroxylated brassinolide analogs used in this study were chemically synthesized according to the method of Hideharu Seto et al. GC-MS analysis was performed on a JOEL Automass JMS-AM 150 mass spectrometer connected to a Hewlett-Packard 5890A-II gas chromatograph. Analysis was conducted under the following conditions: GC column, DB-5 (0.25 mm ×15 m, 0.25-mm film thickness, J&W); injection temperature, 280° C.; carrier gas, helium at a flow rate of 1 mL/min.; ionization, EI (70 eV); column temperature, 80° C. for 1 min., elevated to 320° C. at 30° C./min., then maintained at 320° C. Hydroxylated brassinolide fraction was treated with pyridine containing methaneboronic acid (20 mg per 10 mL) at 80° C. for 30 min. and then with 10 mL of N-methyl-N-trimethylsilyltrifluoroacetamide (MSTFA) at 80° C. for 30 min.

The results of these studies are shown in Table I below:

TABLE I

| i. Brassinosteroid levels (ng/g fresh weight) | phyB-4 | bas1-D phyB-4 |
|---|---|---|
| 6-deoxoTE | 0.19 | 0.26 |
| 6-deoxoCS | 0.79 | 0.04 |
| CS | 0.13 | 0.02 |
| BL | 0.32 | ND | ii.

iii. TE = teasterone; CS = castasterone; BL = brassinolide; ND = not detected.

As shown by the data in Table I, castasterone and 6-deoxocastasterone were detected in bas1-DphyB-4, but at levels greatly reduced compared with those in phyB-4. Moreover, brassinolide was not detected in bas1-DphyB-4. Thus, endogenous levels of BRs in bas1-DphyB-4 were greatly diminished, indicating that this mutation affects BR levels and may be related to hydroxylation of brassinolide. In fact, an increased accumulation of 6-deoxoteasterone was found in the bas1-DphyB-4 mutant.

EXAMPLE 11

Tobacco Transformation

*Nicotiana tabaccum* cv. *Xanthi* was used for transformation. The same *Agrobacterium* strains used for *Arabidopsis* transformation were grown over night until they had reach mid log phase growth. The cultures were diluted 1:10 in sterile water and were co-cultivated for 20 min. with leaf disks from sterile grown young tobacco plants. These disks were incubated on 2×growth media, 0.8% bactoagar (Difco Laboratories, Detroit Mich.) in continuous white light. After 48 hours, leaf disks were placed upside down on fresh plates of the same growth media supplemented with 0.4 mg/L of indoleacetic acid (IAA), 2 mg/L benzyl-aminopurine (h0BAP), 200 mg/L kanamycin and 500 mg/L carbenicillin. This media was replaced every 2 weeks. When shoots formed, they were removed from the leaf disk and placed on fresh media supplemented with just 200 mg/L kanamycin. Once roots formed, plants were transplanted into standard greenhouse conditions and grown until flowering. T2 seeds were sterilized for 30 min. in 10% (v/v) bleach with 0.05% triton X-100 then washed 3 times with sterile water and plated on 2×growth media, 0.8% bactoagar with or without 200 mg/L kanamycin.

While the invention has been described in detail with reference to certain preferred embodiments thereof, it will be understood that modifications and variations are within the spirit and scope of that which is described and claimed.

We claim:

1. A method of producing a genetically modified plant characterized as having dwarf adult stature, said method comprising:
    (a) contacting a plant cell with a vector containing an exogenous nucleic acid sequence comprising at least one structural gene encoding SEQ ID NO: 2, said gene being operably associated with a regulatory sequence that causes overexpression of the gene, to obtain a transformed plant cell;
    (b) producing a plant from said transformed plant cell; and
    (c) selecting a plant exhibiting said dwarf adult stature.

2. The method of claim 1, wherein the regulatory sequence comprises a constitutive promoter or an inducible promoter.

3. The method of claim 1, wherein the nucleic acid further comprises a selectable marker.

4. The method of claim 1, wherein the plant is a dicotyledonous plant, or a monocotyledonous plant.

5. The method of claim 1, wherein said exogenous nucleic acid sequence has the nucleotide sequence of SEQ ID NO: 1.

6. The method of claim 1, wherein said genetically modified plant exhibits green foliage that is darker than a wild-type plant.

7. The method of claim 1, wherein the contacting is by physical means.

8. The method of claim 1, wherein the contacting is by chemical means.

9. The method of claim 1, wherein the plant cell is selected from the group consisting of protoplasts, gamete producing cells, and cells which regenerate into whole plants.

10. The method of claim 1, wherein said nucleic acid is contained in a T-DNA derived vector.

11. A genetically modified plant comprising at least one exogenous nucleic acid sequence encoding a BAS1 polypeptide in its genome, wherein the plant is characterized as having a dwarf adult stature, and wherein the amino acid sequence of said BAS 1 polypeptide is SEQ ID NO: 2.

12. The plant of claim 11, wherein the plant contains multiple exogenous nucleic acid sequences encoding the BAS1 polypeptide.

13. The plant of claim 11, wherein the plant comprises darker green leaves in adult plants in comparison to green leaves in a wild-type adult plant.

14. The plant of claim 11, wherein the nucleic acid sequence has the nucleotide sequence of SEQ ID NO: 1.

15. The plant of claim 11, wherein the exogenous nucleic acid sequence is operably associated with a regulatory nucleic acid sequence.

16. The plant of claim 15, wherein the regulatory nucleic acid sequence comprises a promoter.

17. The plant of claim 16, wherein the promoter is a constitutive promoter.

18. The plant of claim 16, wherein the promoter is an inducible promoter.

19. The plant of claim 11, wherein the plant is a dicotyledonous or a monocotyledonous plant.

20. A seed that germinates into a plant comprising at least one exogenous bas1 nucleic acid sequence in its genome; wherein the plant is characterized as having a dwarf adult stature, wherein said exogenous bas1 nucleic acid sequence encodes SEQ ID NO: 2.

21. The seed of claim 20, wherein the plant comprises multiple exogenous nucleic acid sequences encoding SEQ ID NO: 2.

22. The seed of claim 20, wherein the plant comprises darker green leaves in adult plants in comparison to green leaves in a wild-type adult plant.

23. The seed of claim 20, wherein the bas1 nucleic acid sequence has the nucleotide sequence of SEQ ID NO: 1.

24. The seed of claim 20, wherein the bas1 nucleic acid sequence is operably associated with a regulatory nucleic acid sequence.

25. The seed of claim 24, wherein the regulatory nucleic acid sequence comprises a promoter.

26. The seed of claim 25, wherein the promoter is a constitutive promoter.

27. The seed of claim 25, wherein the promoter is an inducible promoter.

28. The seed of claim 20, wherein the plant is a dicotyledonous plant.

29. The seed of claim 20 wherein the plant is a monocotyledonous plant.

* * * * *